United States Patent [19]
Cantor et al.

[11] Patent Number: 5,849,878
[45] Date of Patent: Dec. 15, 1998

[54] DESIGN AND SYNTHESIS OF BISPECIFIC REAGENTS: USE OF DOUBLE STRANDED DNAS AS CHEMICALLY AND SPATIALLY DEFINED CROSS-LINKERS

[75] Inventors: Charles R. Cantor, Boston, Mass.; Roy S. Chuck, New York; Doris B. Tse, Riverdale, both of N.Y.

[73] Assignee: The Regents of the University of California, Oakland, Calif.

[21] Appl. No.: 481,065

[22] Filed: Jun. 7, 1995

Related U.S. Application Data

[62] Division of Ser. No. 107,186, Aug. 13, 1993, Pat. No. 5,635,602.

[51] Int. Cl.$^6$ .......................... C07K 17/00; C07K 16/46; C07K 19/00
[52] U.S. Cl. ................................. 530/391.9; 530/391.5; 530/391.1; 530/387.3; 536/23.1
[58] Field of Search .......................... 530/391.1, 391.5, 530/391.9, 387.3; 935/6; 536/23.1

[56] References Cited

U.S. PATENT DOCUMENTS

| | | | |
|---|---|---|---|
| 4,650,675 | 3/1987 | Borel et al. | 424/85 |
| 5,078,998 | 1/1992 | Bevan et al. | 424/85.8 |
| 5,391,723 | 2/1995 | Priest | 536/23.1 |

FOREIGN PATENT DOCUMENTS

| | | |
|---|---|---|
| 2058019 | 6/1992 | Canada . |
| 0336379 | 10/1989 | European Pat. Off. . |
| 0491362A2 | 6/1992 | European Pat. Off. . |
| 9311162 | 6/1993 | WIPO . |

OTHER PUBLICATIONS

Kuijpers, W.H.A. et al. 1993. Bioconjugate Chem 4:94–102.
Nakagami, S., et al., OPreparation of Enzyme–Conjugated DNA Probe and Application to the Universal Probe System, 1 *Analytical Biochemistry*, 198:75–79 (1991).
Wong, J.T., et al., OCharacterization of the CD4$^{30}$ and CD8$_8$ Tumor Infiltrating Lymphocytes Propagated with Bispecific Monoclonal Antibodies[1], 1 *The Journal of Immunology*, 143(10):3404–3411 (1989).
Fanger, M.W., et al., OBispecific Antibodies, 1 *Critical Reviews in Immunology*, 12(3,4):101–124 (1992).
Bird, R.E., et al., OSingle–Chain Antigen–Binding Proteins, 1 *Science*, 242:423–426 (1988).
Brennan, M., et al., OPreparation of Bispecific Antibodies by Chemical Recombination of Monoclonal Immunoglobulin G$_1$ Fragments, 1 *Science*, 229:81–83 (1985).
Chuck, R.S., et al., OCD4—T–Cell Receptor Complexes on Human Leukemia T Cells, 1 *Proc. Natl. Acad. Sci. USA*, 87:5021–5025 (1990).
Connolly, B.A., et al., OChemical Synthesis of Oligonucleotide Containing a Free Sulphydryl Group and Subsequent Attachment of Thiol Specific Probes, 1 *Nucleic Acids Res.*, 13:4485–4502 (1985).
Glennie, M.J., et al., OPreparation and Performance of Bispecific F(ab'$_y$)$_2$ Antibody Containing Thioether–Linked Fab'$_y$fragments, 1 *J. Immunol.*, 139:2367–2375 (1987).
Jung, G., et al., OTarget Cell–Induced T Cell Activation with Bi– and Trispecific Antibody Fragments, 1 *Eur. J. Immunol.*, 21:2431–2435 (1991).
Kostelny, S.A., et al., OFormation of a Bispecific Antibody by the Use of Leucine Zippers, 1 *J. Immunol.*, 148:1547–1553 (1992).
Mllstein, C., et al., OHybrid Hybridomas and Their Use in Immunohistochemistry,1 *Nature*, 305:537–540 (1983).
Segal, D.M., et al., ODimers and Trimers of Immunoglobulin G. Covalently Cross–Linked with a Bivalent Affinity Label, 1 *Biochemistry*, 15:5253–5358 (1976).
McGraw–Hill Dictionary of Scientific and Technical Terms, (5th ed. 1993), cover page and p. 231.
Sano, T., et al., OImmuno–PCR: Very Sensitive Antigen Detection by Means of Specific Antibody–DNA Conjugates,1 *Science*, 258: 120–122 (1992).
Haugland, R.P. OHandbook of Fluorescent Probes and Research Chemicals 1 published by Molecular Probes, Inc.: Eugene, OR, pp. 56–62 (1989).
Sano, T., et al., OA Streptavidin Mutant Containing a Cysteine Stretch That Facilitates Production of a Variety of Specific Streptavidin Conjugates, 1 *Bio/Technology*, 11:201–206 (1993).
Gallagher, P.F., et al., OCD4 and CD8 Molecules Can Physically Associate with the Same T–Cell Receptor, 1 *Proc. Natl. Acad. Sci.*, 86:10044–10048 (1989).
Olson, W.K., et al., OThe Translation of DNA Primary Base Sequence into Three–Dimensional Structure, 1 *Comp. Appl. Biosci.*, 4(1):133–142 (1988).

*Primary Examiner*—Toni R. Scheiner
*Attorney, Agent, or Firm*—Karen S. Smith; Flehr Hohbach Test Albritton & Herbert LLP

[57] ABSTRACT

The invention relates to bis-protein-DNA conjugates. A protein having a specific ligand binding activity is covalently linked to each end of a derivatized DNA molecule. These bis-protein-DNA conjugates can be used for immunoassays, PCR assays and measuring distances between proteins at up to 3.4 A resolution. The invention also relates to methods of synthesizing these bis-protein-DNA conjugates. Synthesis of the conjugates entails derivatizing the 5' or 3' end of a DNA oligonucleotide and covalently linking that DNA to a protein. The DNA can be conjugated to the proteins, including antibodies or Fab' fragments, using disulfide bond linkage.

15 Claims, 15 Drawing Sheets

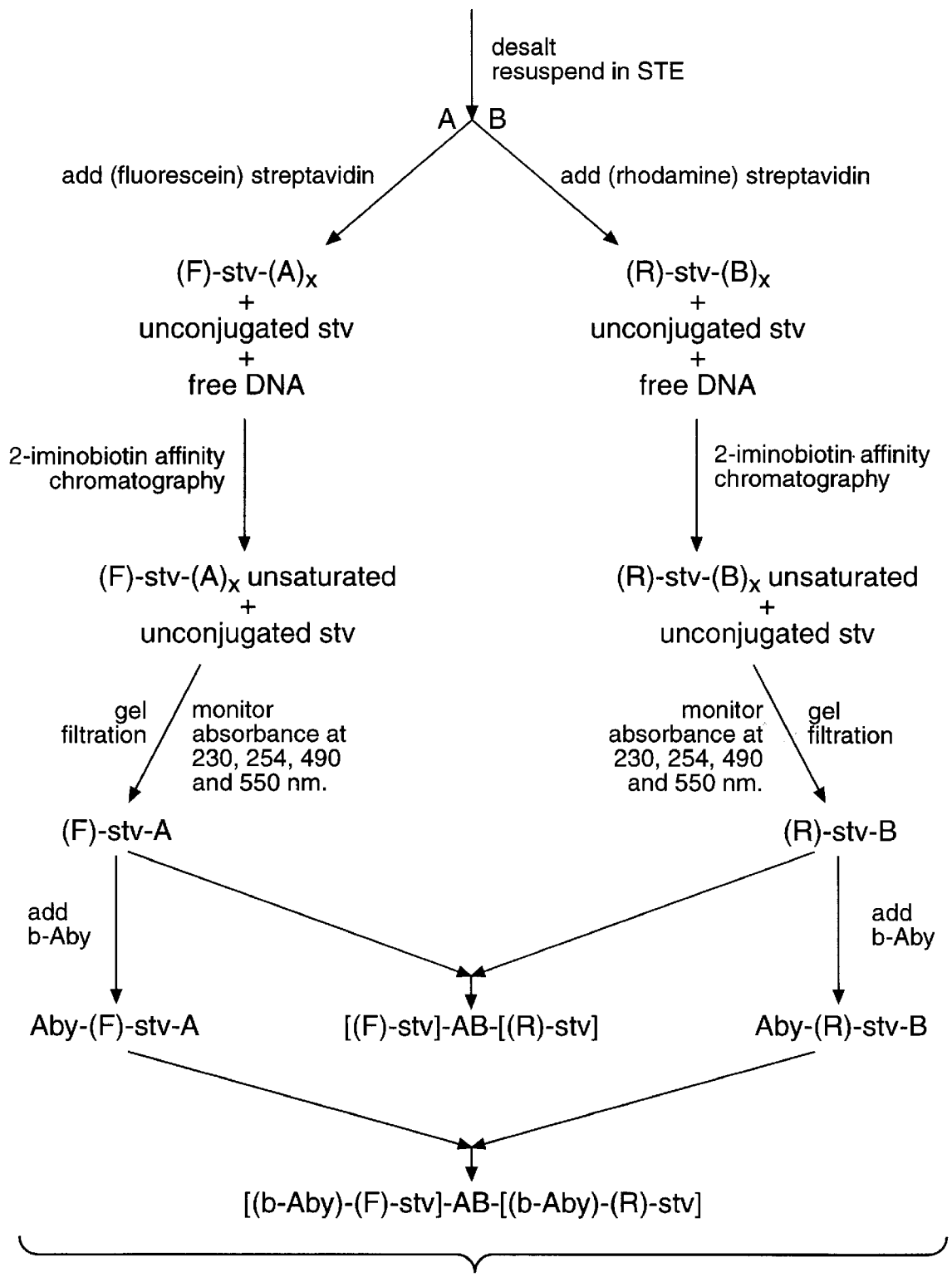
FIG._1

(B = biotin)

```
                              Mae II
                              Ttblll I
                              Aha II
                              Aat II
                              Tag I
                              Sal I
                              HinC II              Mnl I
                              Acc I                Hph I
                              Mae II               Mae III
         5'                   |  || ||    ||   |
         B-ACTATACATCATACGTCGACGTCGTCACCTCA   32
           TGATATGTAGTATGCAGCTGCAGCAGTGGAGT-B
                •  |  || ||•   ||  |  •  5'
                  13                24
                  15                25
                  15                      28
                  15
                  16
                   18
                   18
                   18
                    19
```

Double-stranded DNA

B — Streptavidin          B — Streptavidin

FIG._2

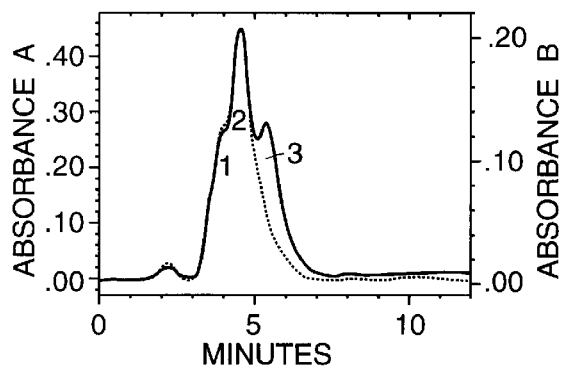
FIG._3A
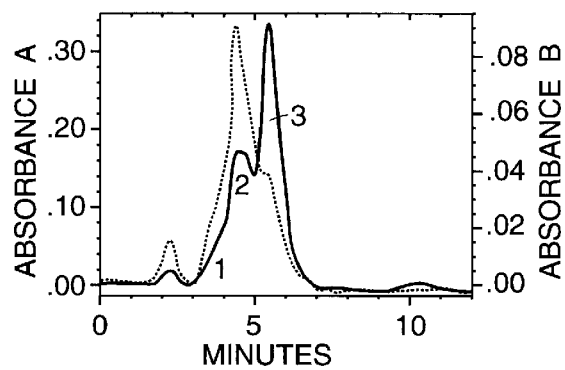
FIG._3B
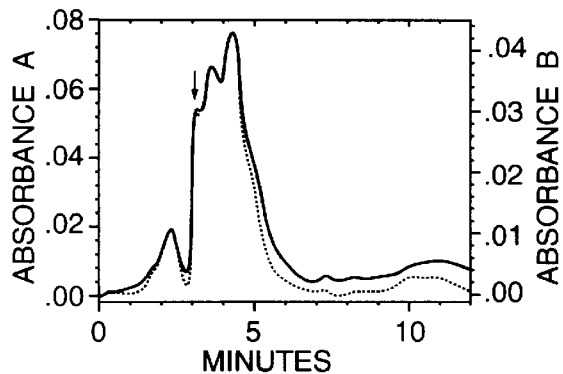
FIG._3C
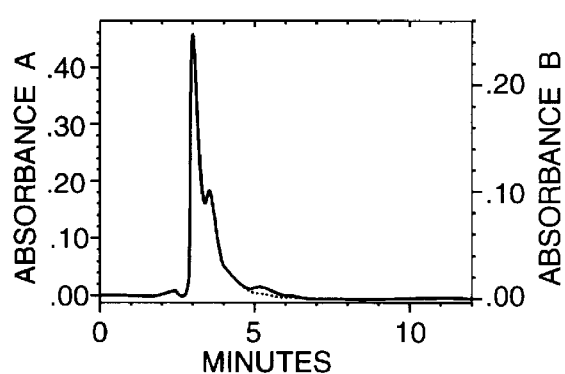
FIG._3D
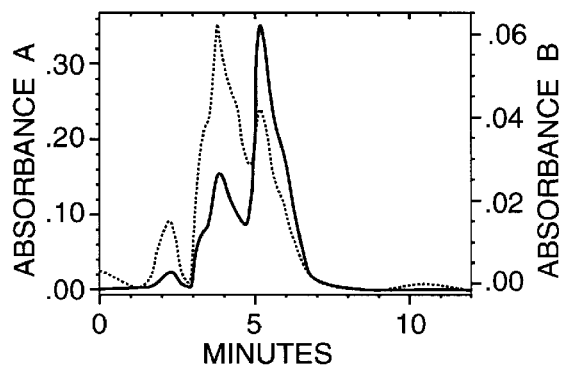
FIG._3E

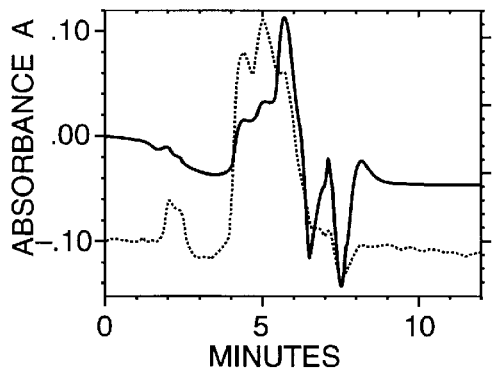
FIG._4A
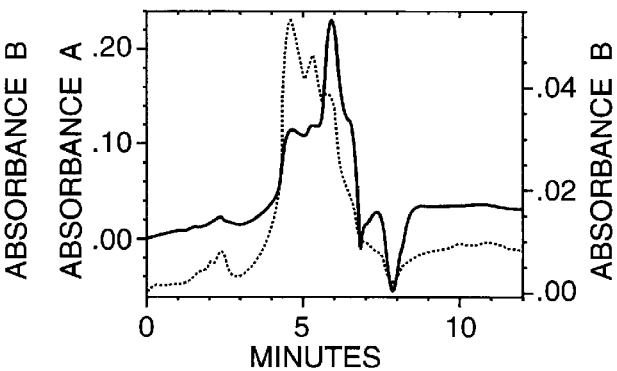
FIG._4B
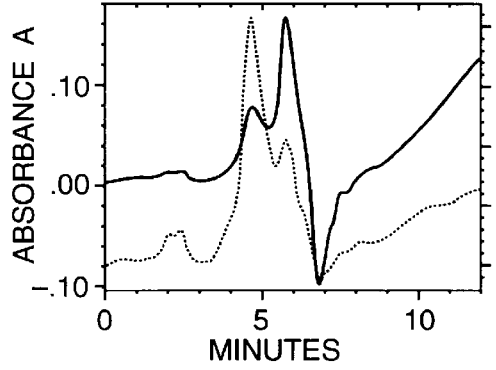
FIG._4C
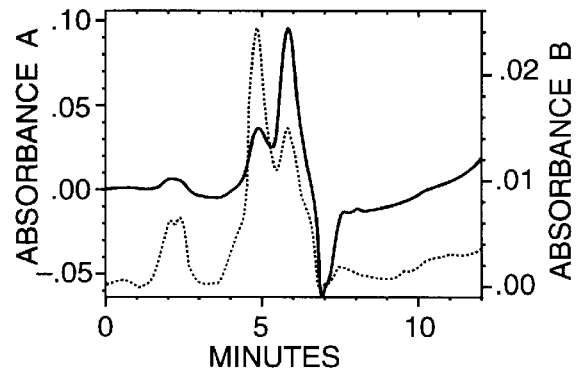
FIG._4D
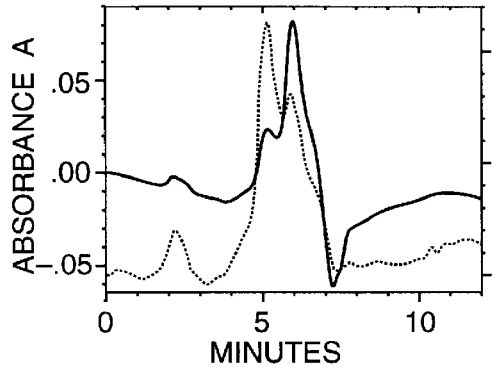
FIG._4E
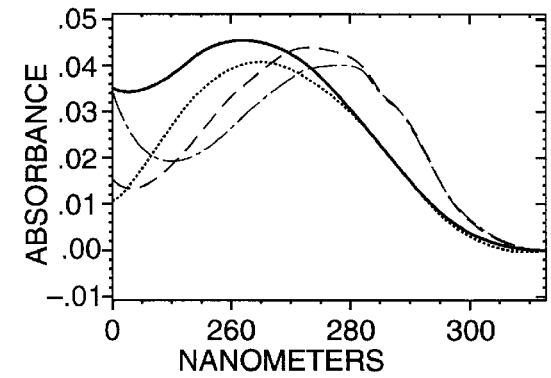
FIG._4F

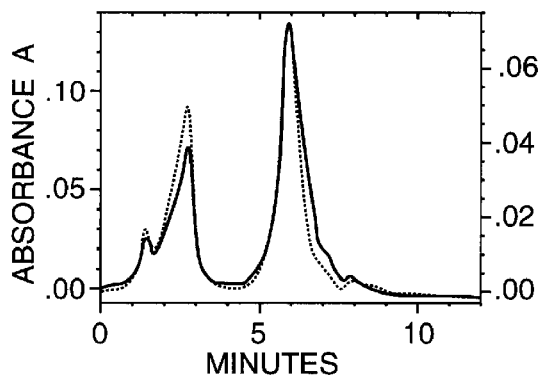
FIG._5A
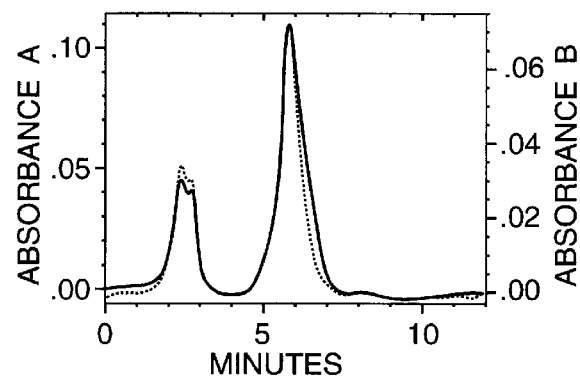
FIG._5B
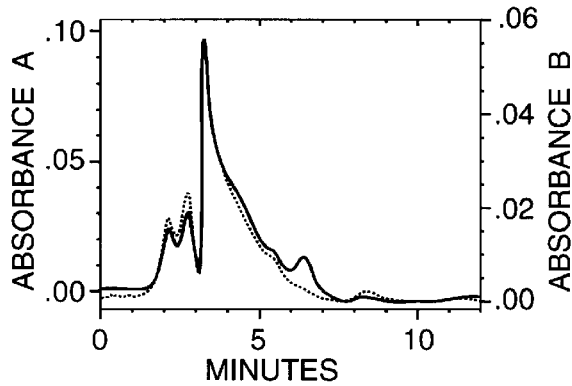
FIG._5C
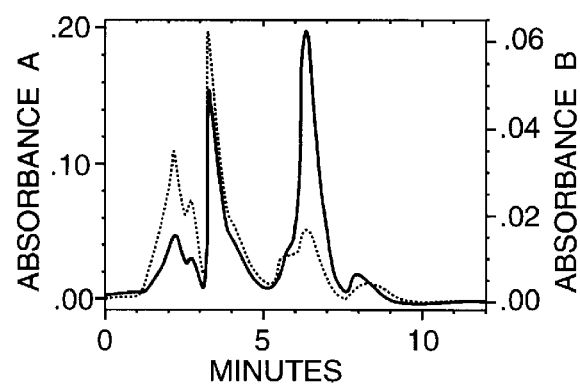
FIG._5D
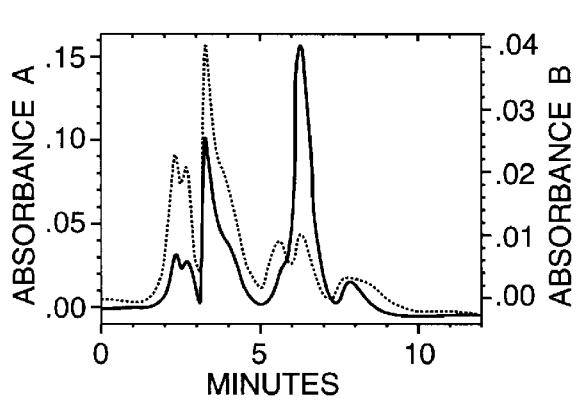
FIG._5E
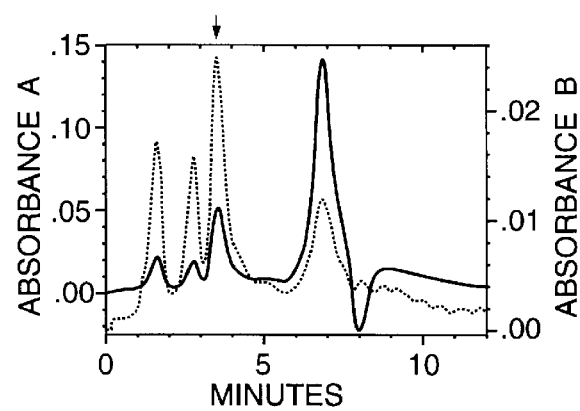
FIG._5F

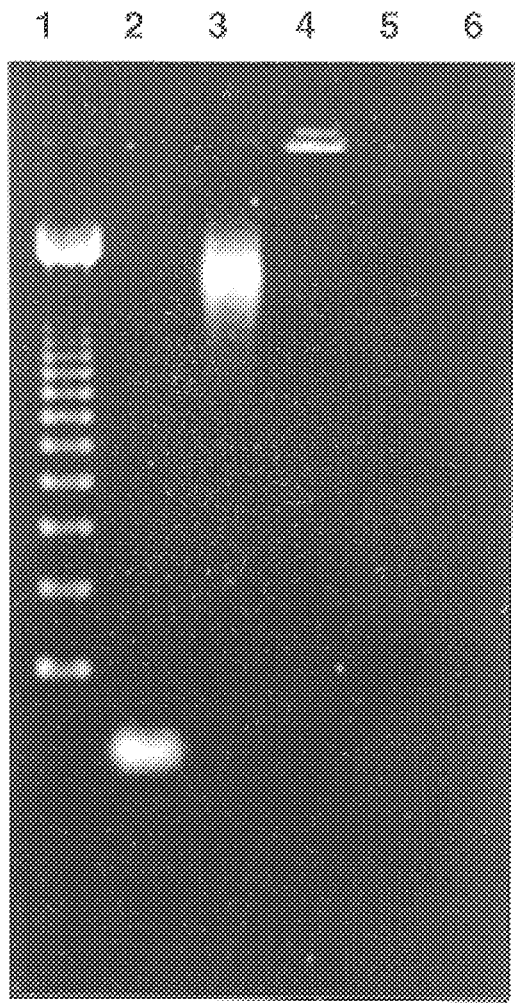
FIG._6

FIG._7

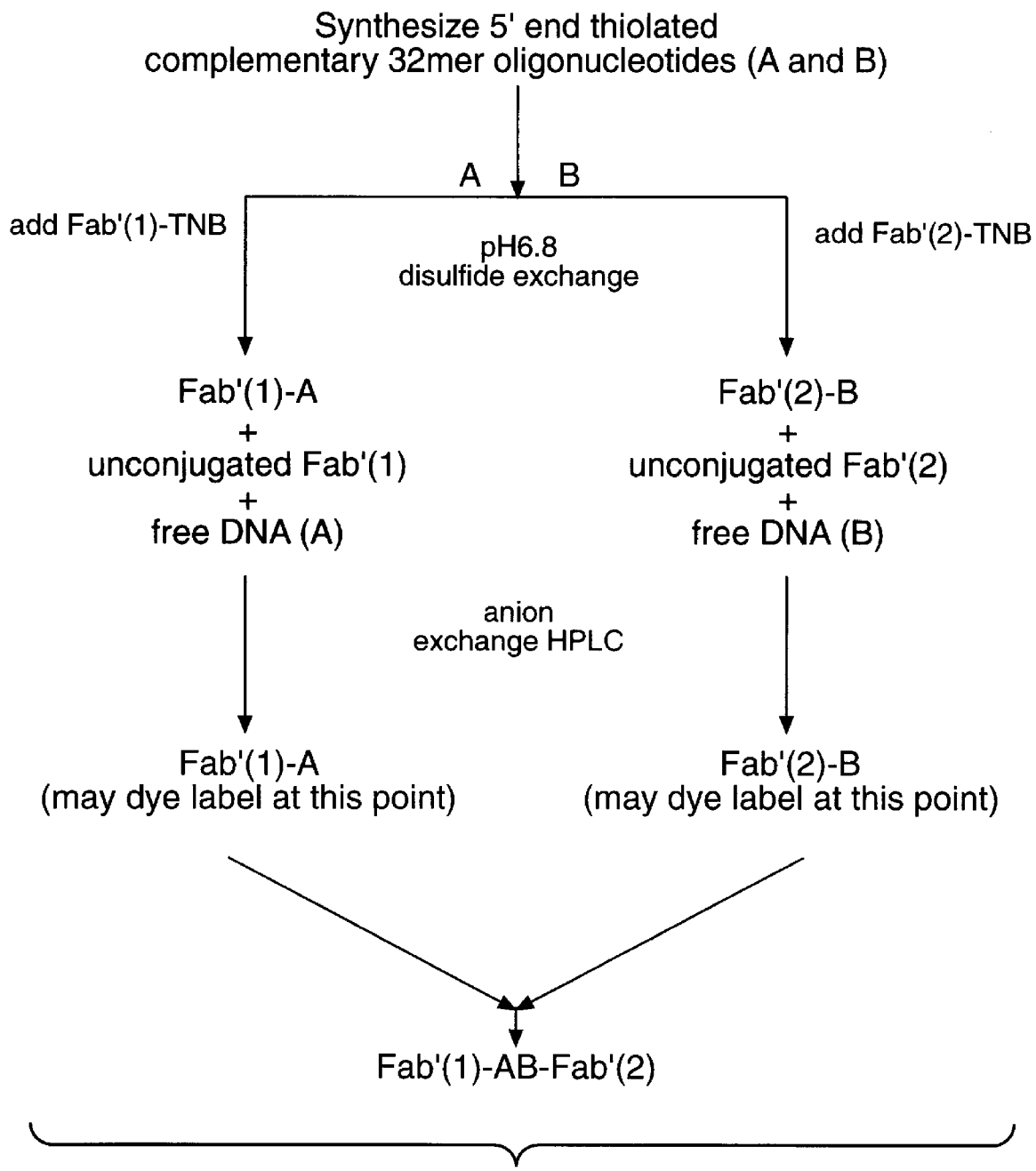
FIG._8

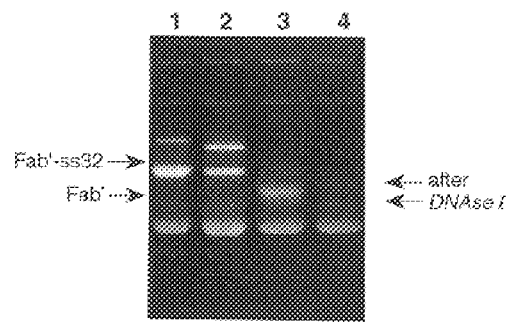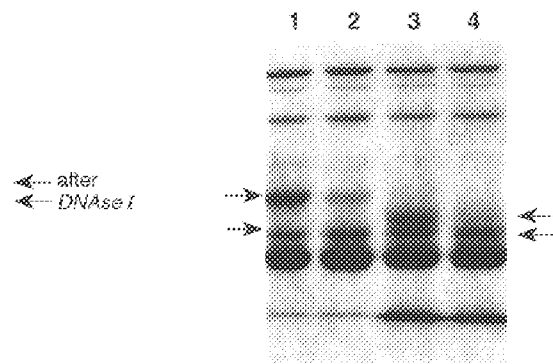
FIG._9A  FIG._9B  FIG._9C

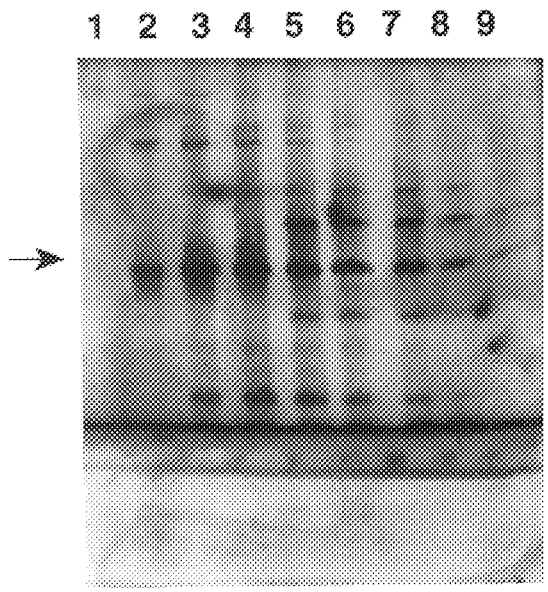
FIG._10A
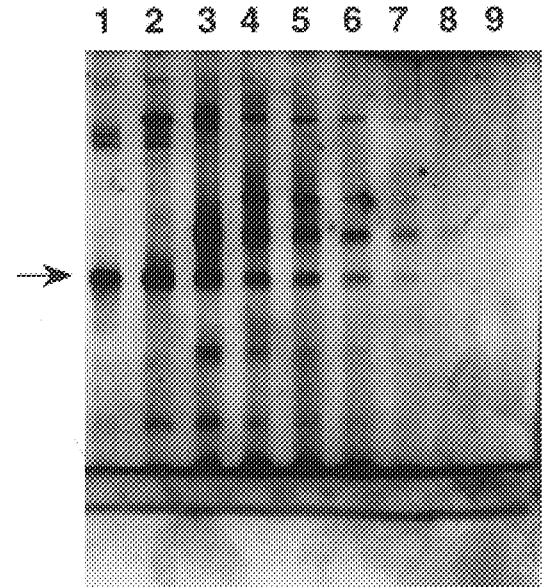
FIG._10B
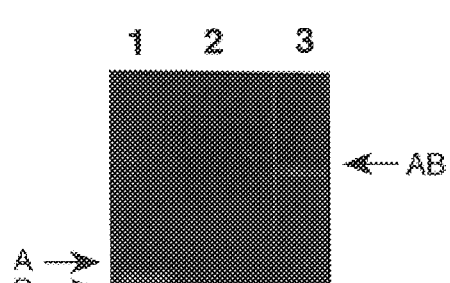
FIG._10C
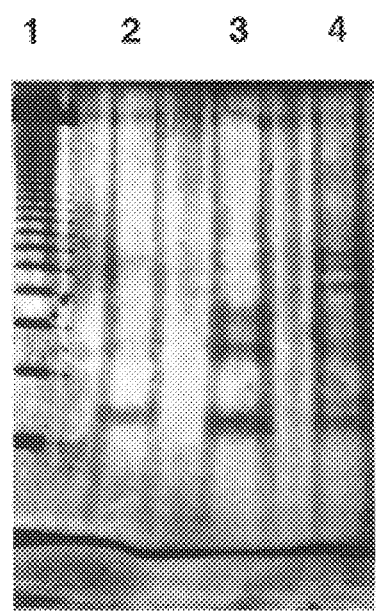
FIG._10D

Mouse IgG immobilized onto nitrocellulose membrane which was subsequently blocked and washed

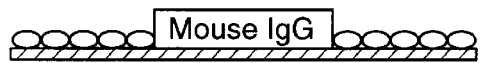

Label membrane with unpurified polyclonal goat anti-mouse IgG Fab'-single-stranded 32mer oligonucleotide conjugate Wash membrane to remove unbound species

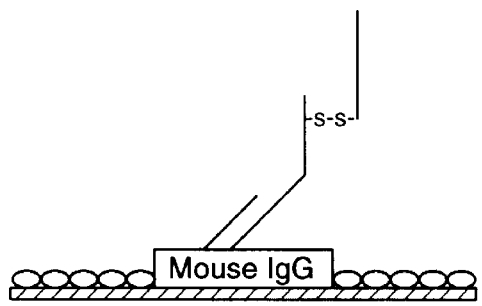

Label with purified streptavidin-single-stranded complementary 32mer oligonucleotide conjugate
Anneal at room temperature
Wash membrane
Label with biotinylated peroxidase
Detect with chemiluminescence

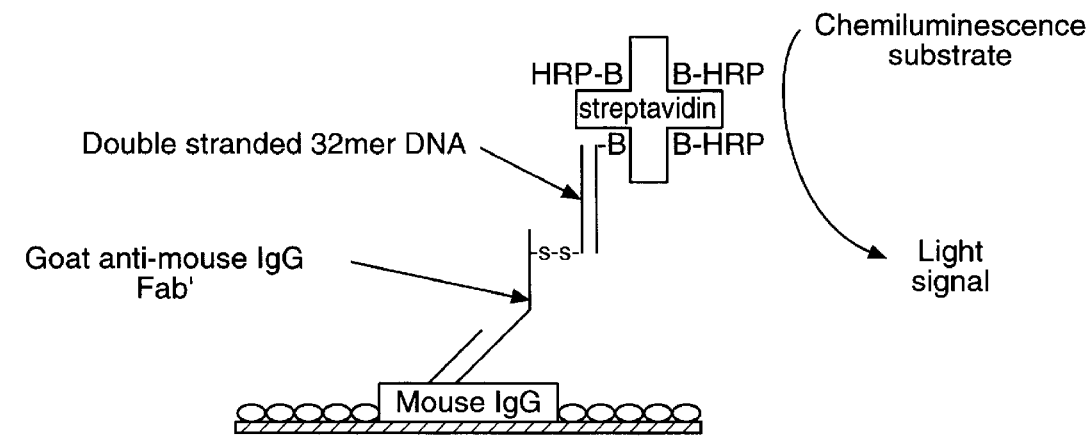

FIG._11

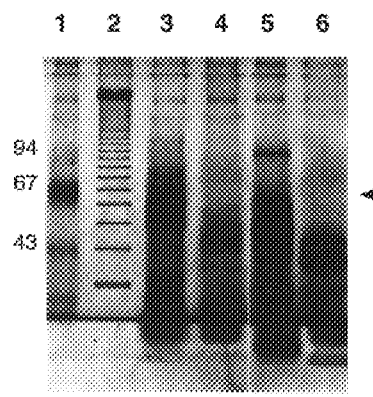
FIG._12A
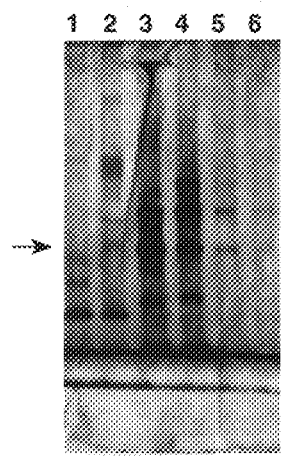
FIG._12B
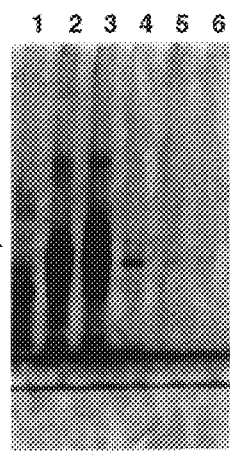
FIG._12C

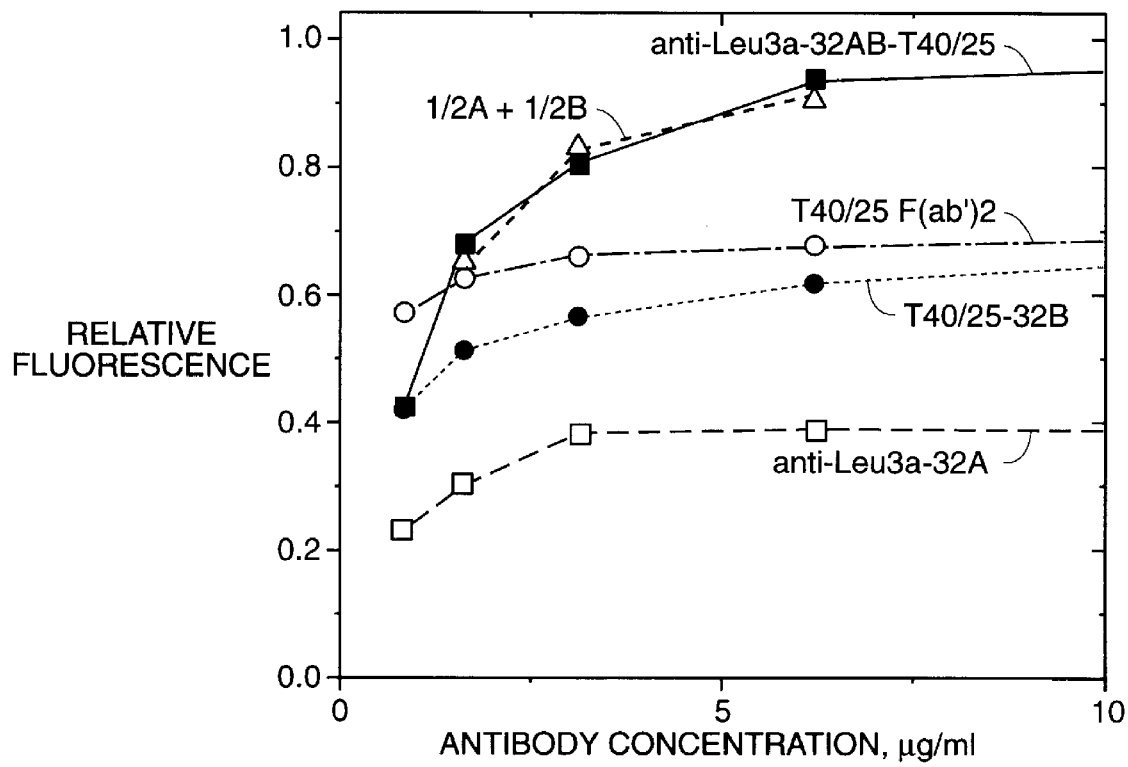
FIG._13A
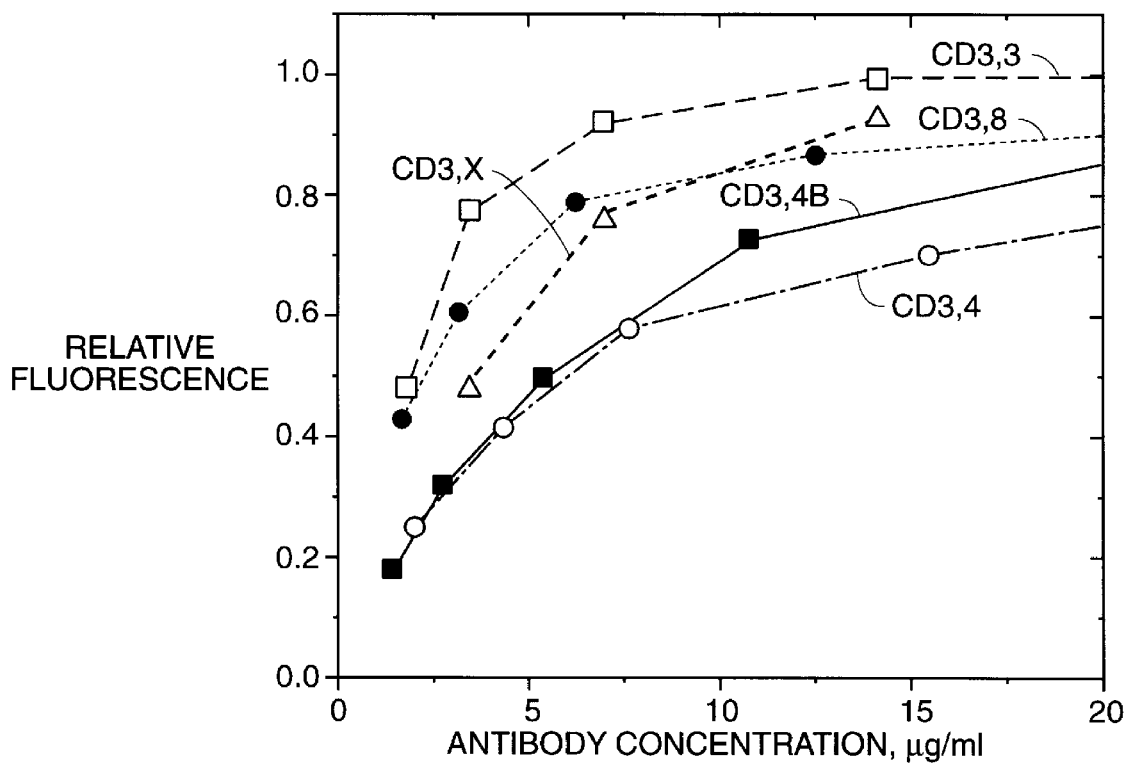
FIG._13B

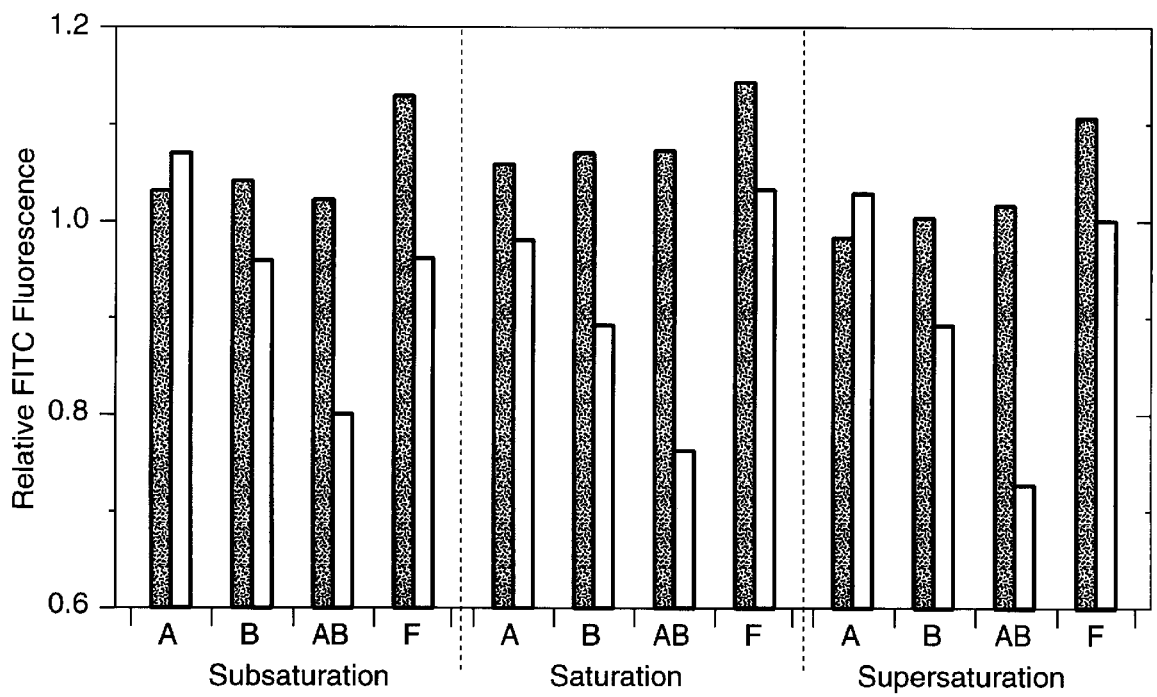
FIG._14A
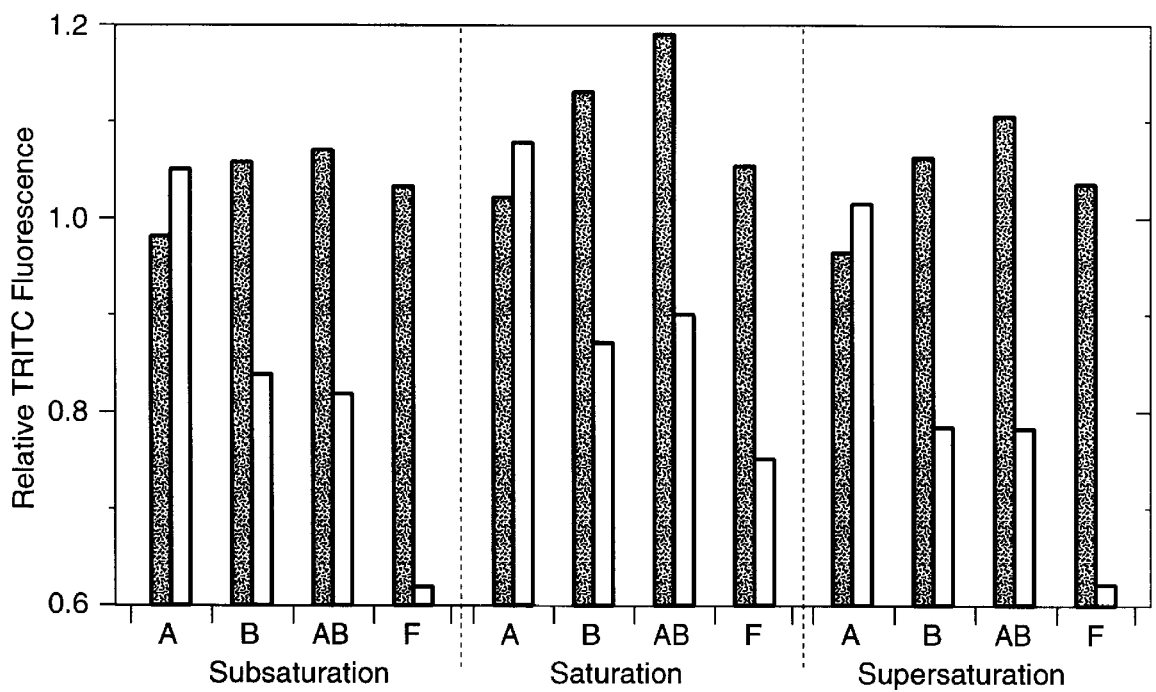
FIG._14B

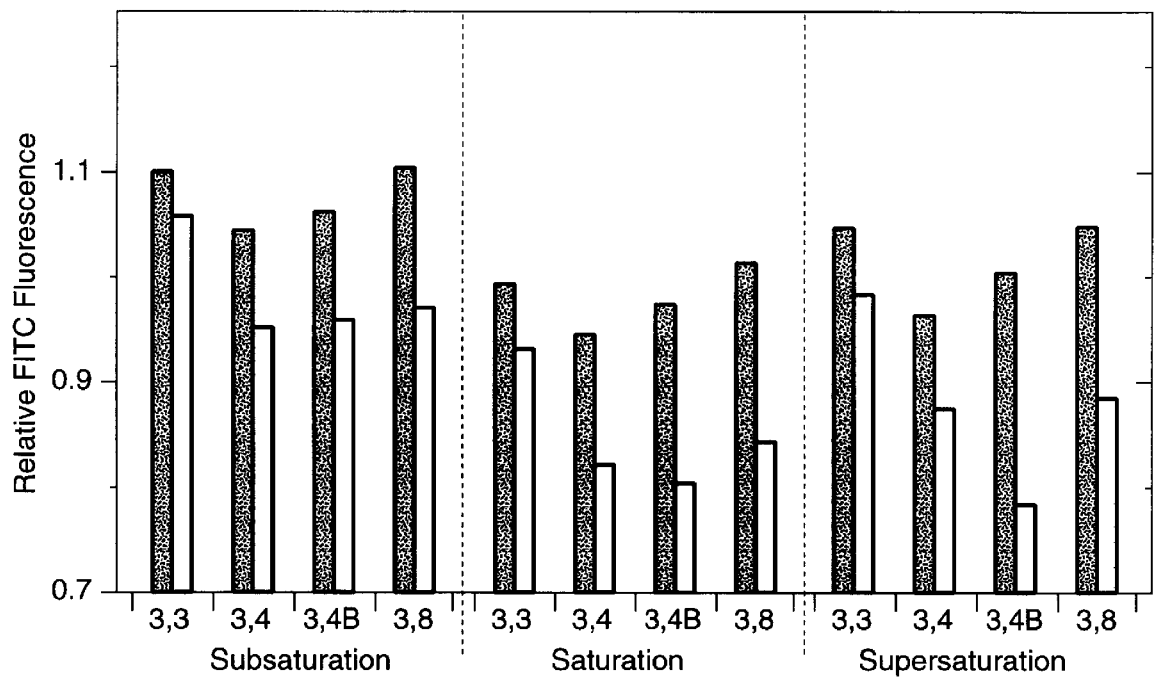
FIG._14C
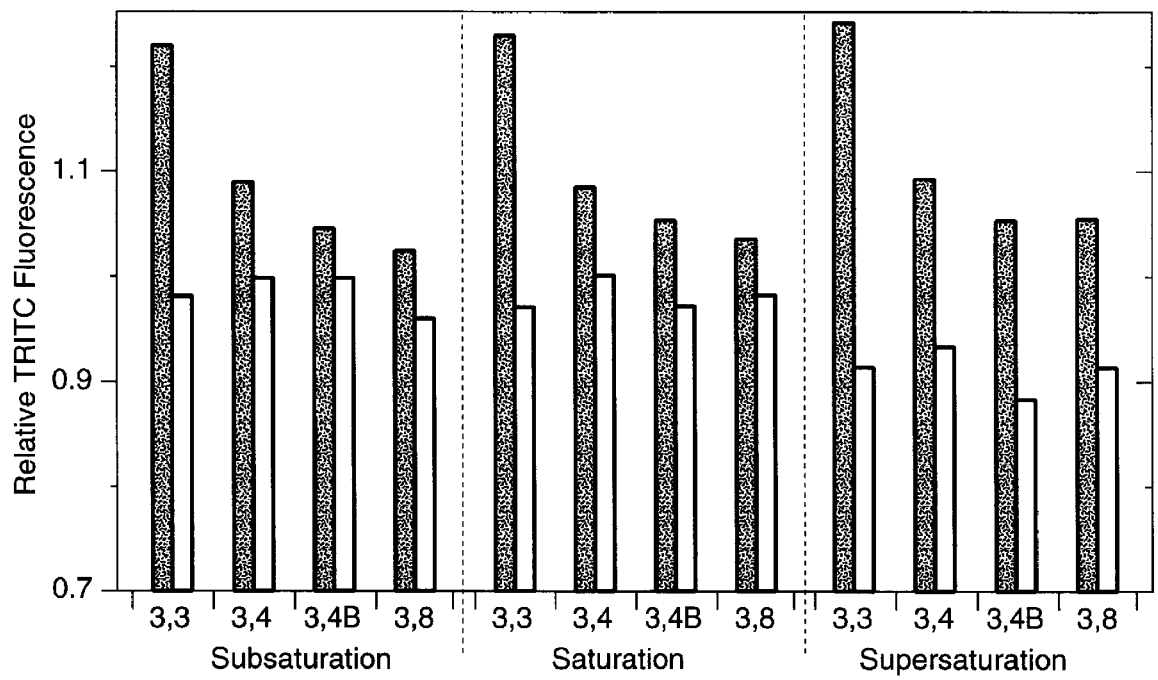
FIG._14D

DESIGN AND SYNTHESIS OF BISPECIFIC REAGENTS: USE OF DOUBLE STRANDED DNAS AS CHEMICALLY AND SPATIALLY DEFINED CROSS-LINKERS

This is a division of application Ser. No. 08/107,186 filed Aug. 13, 1993, now U.S. Pat. No. 5,635,602.

ACKNOWLEDGEMENT

This invention was made with Government support under Grant Contract No. CA39782 awarded by the National Institutes of Health. The Government has certain rights in this invention.

TECHNICAL FIELD

This invention relates to bispecific antibodies and antibody conjugates and is particularly directed to bis-antibody double stranded DNA conjugates and bis-Fab' double stranded DNA conjugates and their use in the recognition of immobilized antigens and the characterization of relationships between cellular proteins. The invention further relates to immunoassays using the DNA conjugates.

BACKGROUND

Antibodies are powerful tools for molecular and cellular analysis and for clinical diagnosis. The power comes from the considerable specificity of antibodies for their particular epitopes. This allows the detection or purification of a single species from among a very large background of competitors. The power of antibodies as a tool is enhanced by the ability to produce monoclonal antibodies against most desired antigens and to engineer antibodies further by recombinant DNA methods.

DNA molecules are also powerful tools for the analysis of molecules and cells and for clinical diagnosis. The power of DNA resides in the great specificity of stringent hybridization which allows about any unique DNA sequence to be detected specifically or, in principle, isolated. The power of DNA as a molecular tool is enhanced by the ability to make virtually any DNA sequence by automated methods and to amplify any DNA sequence from microscopic to macroscopic quantities by the polymerase chain reaction. Another very attractive feature of DNA is the great rigidity of short double helices. As judged by hydrodynamic criteria, DNA molecules of 30 to 60 base pairs are essentially rigid rods as far as flexure perpendicular to the helical axis is concerned. There is torsional flexibility, however, so that considerable rotation around the helical axis should be possible.

Many plausible mechanisms for environmental modulation of cell action or for cell-cell intimacy are based on alterations of distances between proteins at the cell surface. It is difficult to study or manipulate these distances because some of the molecules of interest are very rare, and most of the distances are too long to be observed by ordinary physical or chemical techniques.

One approach to solving these problems has been to use bispecific antibodies. In addition to hybrid hybridoma or "quadroma" generation (Milstein and Cuello, 1983), bispecific antibodies may also be created via chemical cross-linkage. Of the many methods available, disulfide exchange between reduced hinge region sulfides of antibody Fab' fragments may prove to be the most efficient in terms of both yield and defined homogeneity of product (Brennan et al., 1985). However, this and most other current cross-linking methods lack the option of varying the relative 3-dimensional spatial orientation of the 2 antigen combining sites. Of note, though, is the current strategy employed by Kostelny et al. (1992) in which they expressed 2 different Fab'-leucine zipper (derivatives of Fos and Jun) fusion proteins in mouse myeloma cells to form 2 separate $F(ab'\text{-zipper})_2$ homodimers, reduced them in vitro, and then mixed them to efficiently form $F(ab'\text{zipper})_2$ heterodimers, to provide a resultant specific antibody of some defined structure.

The proper functioning of a cell depends on the interaction of the various components on the surface of that cell. It has been shown that CD4 may act to increase affinity of the T cell for class II MHC expressing cells by direct binding to class II (Doyle and Strominger, 1987). Moreover, it may also act synergistically with the TCR in a signaling capacity (Fleischer and Schrezenmeier, 1988). Various other studies have directly shown that subsets of CD4 and the TCR are in close association with each other on the cell surface (For example, see Gallagher et al., 1989; Chuck et al., 1990). Still others have demonstrated that CD4 and the TCR may bind to the same class II MHC molecule (Miceli et al., 1991). These data imply that CD4 is probably both physically and functionally linked to the TCR.

Many studies have shown that T cells may be triggered via certain anti-receptor monoclonal antibodies, including those against CD4 and the TCR (for example, see Haque et al., 1987; Janeway et al., 1987).

In an approach to examine the association between CD4 and the T cell receptor (TCR) on the cell surface. T cells were triggered with hetero-cross-linked anti-CD4 and anti-TCR antibodies. It was found that the heterocombination triggers much more efficiently than the homo-combinations unlinked antibodies (Ledbetter et al., 1988). These results were used as indirect evidence for functional as well as physical associations between 2 T cell surface molecules. However, no one has yet investigated the actual role that distance may play in effecting such hetero-cross-links, since long range cross-linkers do not exist.

In the previous experiments in which T cells were triggered via the CD4:TCR complex, workers used either solid state supports such as microbeads, secondary antibodies or chemical cross-linkers to cross-link anti-CD4 to anti-TCR. In such studies the relative positions of the two different triggering antibodies were largely unknown. Further, in the study using microbeads it was impossible to tell how many receptors were aggregated by the beads at the cell contact point. Therefore, the functionality of the CD4-TCR physical association has yet to be explored. Relative position information would be useful in dissecting the geometry of the putative CD4:TCR activation complex since the distance separating CD4 and TCR cannot be accurately determined even by energy transfer measurements. One question is whether CD4 needs to be close to the TCR, i.e., act as a co-receptor during the process of antigen recognition (Janeway, 1988) which may include presentation of $p56^{lck}$ and other kinases to CD3:TCR (Haughn et al., 1992), or whether it can just as well assert its synergistic action over a longer distance.

Accordingly, there exists a need for a better technique for precisely measuring the distance between proteins on cells and for a different means for varying and controlling the three dimensional spatial separation of combining sites in bispecific antibodies.

Further, most immunoassays do not allow for the detection of a single molecule in a sample. Therefore, a need exists for more methods that can accurately detect single molecules in a sample.

Also there exists several instances where the polymerase chain reaction has been combined with other immuno techniques to identify various entities such as viruses and bacteria in a sample. However, most of these techniques as well as other common immunoassays are capable of detecting the presence of only a single analyte in a sample. Therefore, there also exists a need for an assay which will coincidentally detect more than one analyte such as pairs of viral antigens in a single sample.

BRIEF SUMMARY OF THE INVENTION

The present invention provides novel DNA antibody and DNA antibody fragment conjugates. In particular, the invention comprises bis-conjugates of antibodies or antibody fragments, especially Fab' antibody fragments, cross-linked by an end-derivatized double stranded DNA. The conjugates can comprise homo- or hetero-, bi-, tri- or tetra-specific antibodies and the DNA can contain one or more restriction enzyme sites. The invention provides general techniques for preparing the double stranded DNA-antibody and double stranded DNA-antibody fragment conjugates and for using them to measure the distance and study the relationship between cell surface proteins. The invention also provides an immunoassay using part of the technique for preparing the conjugates and a method for using the DNA-conjugates in immuno-PCR assays to coincidentally detect more than one antigen in a sample.

BRIEF DESCRIPTION OF THE DRAWINGS

FIG. 1 is a diagrammatic representation of the method for synthesizing a bis(streptavidin-antibody)-double stranded 32 base pair DNA (SEQ ID NOS:1 and 2).

FIG. 2 shows the nucleotide sequence of a 5' biotinylated complementary 32mer DNA (SEQ ID NOS:1 and 2) used to cross-link two streptavidin molecules, a restriction map of that sequence and the general structure of the DNA cross-linked to the two streptavidin molecules.

FIGS. 3A through 3E show HPLC gel filtration traces of reaction products resulting from the purification of biotinylated DNA-streptavidin conjugates.

FIGS. 4A through 4F depict a series of graphs showing the spectral absorbency of single DNA-conjugated and unconjugated streptavidin prepared by gel filtration in buffer having different NaCl concentrations and another graph showing the comparison of the UV absorption spectra of the DNA conjugate and unconjugated streptavidin prepared at various NaCl molarities.

FIGS. 5A through 5F show HPLC gel filtration traces of a bis-(streptavidin-antibody)-double stranded 32 base pair DNA (SEQ ID NOS:1 and 2) conjugate and its constituent reactants before and after annealing.

FIG. 6 is a photograph of a UV excited ethidium bromide stained electrophoretic agarose gel showing the mobilities of a bis-(streptavidin-antibody) conjugated double stranded 32mer (SEQ ID NOS:1 and 2) and its various components.

FIG. 7 is a uranyl acetate negatively-stained transmission electron micrograph of bis-(streptavidin-antibody)-double-stranded 32 base pair DNA (SEQ ID NOS:1 and 2).

FIG. 8 is a diagrammatic representation of a method for synthesizing 32mer DNA (SEQ ID NOS:1 and 2) cross-linked Fab' antibody fragments.

FIGS. 9A through 9C depict photographs of stained SDS-PAGE gels showing the mobilities of various conjugated and unconjugated Fab' fragments before and after treatment with various enzymes.

FIGS. 10A through 10D depict photographs of stained SDS-PAGE gels depicting the mobilities of GA2 (anti-Class I MHC) Fab'-oligonucleotide conjugates and their precursors and components.

FIG. 11 is a diagrammatic representation of a scheme for detecting immobilized mouse IgG with a polyclonal goat anti-mouse IgG Fab' double stranded 32mer-streptavidin (SEQ ID NOS:1 and 2) conjugate and biotinylated horse radish peroxidase.

FIGS. 12A through 12C depict photographs of a series of stained SDS-PAGE gels showing the mobilities of a heterobispecific antibody Fab'-32mer double stranded DNA (SEQ ID NOS:1 and 2) conjugate and its individual constituents and precursors.

FIGS. 13A and 13B depict two graphs showing the HPB-ALL cell binding curves for DNA-antibody and hybrid antibody conjugates.

FIGS. 14A through 14D depict a series of bar graphs showing the CD4 and CD3 modulation capabilities of different DNA-antibody and hybrid antibody constructs under subsaturating, saturating and supersaturating conditions after 0° C. pre-binding, unbound antibody removal, and then 37° C. incubation.

DESCRIPTION OF THE SPECIFIC EMBODIMENTS

This invention is directed to the use of double stranded DNA as a cross-linking agent between antigen binding proteins such as antibodies or antibody fragments to form DNA-antibody conjugates. When two antibody binding sites are tethered at the ends of a short DNA duplex, they are able to reach similarly spaced ligands with out much inhibition by ligand geometry, other than the distance separating them. Further, when the DNA cross-linking molecules are of defined lengths they provide suitable tools for cross-linking and for measuring the distance between cell surface components. The rigidity of double-stranded DNAs in the hundred base pair size range (Hagerman, 1988) and the ability to synthesize any such molecule of interest permits the use of DNA as a set of molecular rulers with sizes up to several hundred Å with a resolution of about 3 Å. Each base pair is approximately 3.4 Å in solution and a 32mer double stranded DNA therefore is about 100 Å long.

In order to cross-link two antigens on a cell surface the entire bis antibody-DNA conjugate must be approximately the same length as the distance between the two antigens. The length is approximate because the antibodies and the Fab' antibody fragments can flop or swivel back and forth at the ends of the DNA cross-linker. A Fab' antibody fragment is about 50 Å in diameter. Therefore, if the DNA linker is for example 100 Å long and the two Fab' fragments are positioned such that they are sticking straight out, the length of the conjugate would be 200 Å long. However, if the Fab' fragments are flopping (i.e., oriented) inward, they each may extend outward for only 40 Å and the length of the total conjugate may only be about 180 Å long. There is also the possibility that the two fragments may not extend outward at all. If the distance between the two antigens to be cross-linked is 200 Å and the Fab' fragments are inclined inward and are only extending outwards at 40 Å each as described above, the DNA strand may have to be 120 Å long in order to cross-link the two antigens.

A special advantage of using DNA as a molecular scaffold for constructing arrays of other molecules is that one is not limited to DNA with 2 ends. For example, 3 and 4 ended junctions have been made and they can form the basis for an endless array of more complex structures. Therefore, tri- and tetra-specific antibodies can be prepared using other higher order DNA structures such as Holliday junctions in conjunction with the methods provided below for preparing bi-specific antibodies. In addition, numerous proteins are known with very specific DNA binding sites. Such proteins can augment and enhance the methods for starting with DNA and producing a specific assembly of other molecules.

The length of the double stranded DNA used to form the cross-linking agent between the antigen binding proteins can be from about 2 to about 100 base pairs, more preferably from about 10 to about 80 base pairs, most preferably from about 20 to about 60 base pairs.

The invention provides for homo-bis-antibody-DNA conjugates (i.e., DNA cross-linked to antibodies having the same antigen specificity) as well as hetero-bis-antibody-DNA conjugates (i.e., DNA cross-linked to antibodies having different antigen specificities). Homo-bis-antibody-DNA conjugates, when used in immunoassays, provide an advantage over most antibodies similarly used in that the antibodies in the DNA conjugates may bind more strongly due to cooperation and can be defined in three dimensions.

Although the words used herein have their usual meanings when applied generally to the invention, reference to a molecule or part of a molecule "linked" or "attached" to another molecule or part usually but not necessarily means covalently bonded. "Bound" includes both non-covalent and covalent associations. It is preferred that non-covalent associations be sufficiently stable so as not to appreciably dissociate during an assay such as an immunoassay.

To prepare the DNA conjugates of the invention, the 5' ends of the DNA are preferably derivatized either by streptavidin or avidin or by thiolating those ends and consequently binding the derivatized ends to the appropriate derivatized antibodies by means of streptavidin/biotin or avidin/biotin binding or disulfide bond formation, respectively. Even though biotin/streptavidin and disulfide bond formation are the preferred methods for conjugating the DNA to antibodies, other known methods of chemical cross-linkage may also be used. Also, since DNA derivatized at the 5' ends was the DNA most readily available, it was the DNA used in the examples. However, DNA that has been derivatized at the 3' ends can also serve as an acceptable cross-linker.

In conducting the studies in the Examples, a 32 base pair DNA (SEQ ID NOS:1 and 2) sequence was chosen because it corresponds to approximately 3 complete turns of the B-form helix, placing the 2 5' ends approximately in cis, and because it is inexpensive to synthesize in large amounts. It was designed to contain a Sal I restriction enzyme cleavage site in the center. Sal I was chosen because, unlike many other restriction enzymes, its cleavage activity does not require addition of reducing agents which can potentially damage antibodies, and because it also is inexpensive. However, the DNA sequence used as the cross-linker may contain the cleavage sites of a variety of enzymes provided cleavage does not require reducing agent. Other design criteria used in choosing the DNA sequence were minimization of both single-stranded secondary structure and double-stranded curvature to ensure synthesis of a straight and maximally rigid cross-linker. Single-stranded DNA structure was examined using Tinoco energy rules (Williams and Tinoco, 1986). Double-stranded curvature was examined using the program of Olson and Srinivasan (Olson and Srinivasan, 1988).

If the 5' ends of the DNA are derivatized by streptavidin, the appropriate antibodies or antibody fragments are also biotinylated and the derivatized DNA subsequently binds to the derivatized antibody by means of biotin/streptavidin binding. A good discussion of the streptavidin/biotin system and other appropriate methods of conjugation, as well as general immunoassay techniques, can be found in Tyssen, P. (1988) *Practice and Theory of Enzyme Immunoassays* 15, New York: ELSEVIER. Streptavidin is a 60 kDa protein made up of 4 identical biotin binding-subunits with a $K_d$ of $10^{-15}$M (Hofmann et al., 1983). Streptavidin is widely used for the detection of a variety of biotinylated substrates. Streptavidin has less non-specific binding than eukaryotic avidin since it is not glycosylated and is preferred over avidin for preparing the DNA conjugates of the invention. To prepare the conjugates 5' end-biotinylated complementary oligonucleotides of anywhere from about 2 to about 100 bases are synthesized via standard automated β-cyanoethyl phosphoramidite DNA synthesis using a biotin phosphoramidite as provided by Applied Biosystems, Foster City, Calif. Each strand is then reacted sequentially with streptavidin and a biotinylated antibody or biotinylated antibody fragment before forming the desired bis-(streptavidin-antibody)-double-stranded DNA conjugate via a DNA annealing reaction. Alternatively, annealing can be performed without biotinylated antibody binding to create the general biotinylated substrate cross-linker, bis-streptavidin-double-stranded DNA.

In the initial attempts to synthesize DNA-antibody cross-links, a variety of direct chemical cross-linking agents proved unsuccessful. These studies were plagued by inefficient cross-linking (especially in the case of antibody Fab' fragments) difficulty in separating free DNA from products and other reactants by gel filtration, and loss of antibody-antigen binding activity. Use of streptavidin overcame these problems. That is, streptavidin as an intermediate cross-linking molecule between biotinylated antibody and biotinylated DNA provided several advantages: gentle and efficient conjugation; the possibility of monitoring the conjugation with dye-labeled reagents; and efficient purification through use of affinity chromatography with 2-iminobiotin followed by standard gel filtration. However, additional geometric uncertainty and molecular weight introduced by streptavidin complex could prove to be troublesome. The multi-valence of streptavidin may also be troublesome for some applications compared to the bivalence of many chemical cross-linkers since these conjugates are big entities. Helpful, though, is the fact that a variety of proteins can be gently biotinylated, sacrificing little biological activity.

The conjugates of the invention particularly cross-link antigen binding proteins. Almost any antibody or type of antibody can be used in making the conjugates but when specificity is desired preferably the antibody is a monoclonal antibody. Antibody production for use in the invention can be conventional and is not described here in detail. Methods for producing antibodies are well known in the literature and are exemplified by the publication. *Antibodies: A Laboratory Manual* (1988) eds. Harlow and Lane, Cold Spring Harbor Laboratories Press. Particular examples of the numerous antigen binding proteins that can be cross-linked by the DNA conjugation method of the invention include mouse, rabbit, or goat-anti-human IgG, IgA, IgM, IgD and IgE and antibody fragments such as Fab' fragments of IgG1, IgG2a and IgG2b, particularly mouse IgG1 anti-human MHC class I (GA2), anti-CD4 and anti-CD3. Also suitable are *E. coli*-generated antibodies and antibody fragments (Huse et al., 1989; Sastry et al., 1989; Ward et al., 1989), artificial single chain antigen binding proteins (Bird et al., 1988) and non-peptide antibody complementarily-determining region mimetics (Saragovi et al., 1991) resulting in engineered antibody-like molecules created by both molecular biology and synthetic chemistry.

In order to construct hetero-specific, bi-, and higher valent molecules, other workers have utilized both chemical cross-linking (Segal and Hurwitz, 1976) and hybrid hybridoma (Milstein and Cuello, 1983) techniques. However, such methods suffer from the problem of low yield, as well as restricted spatial separation of the different antigen binding sites. The use of 5' end-derivatized bis-streptavidin-double-stranded DNA as a cross-linking molecule for biotinylated antibodies overcomes these limitations and further expands the utility of hetero-specific antigen binding proteins. Using such a cross-linking molecule offers the following advantages: (1) rigidity in the hundred base pair size range, (2) the ability to synthesize any DNA molecule of interest, (3) the ability to control the relative 3-dimensional spatial, i.e., both angular and linear, positions of the 2 ends by varying either the number of base pairs, the base sequence, or the amount of unwinding intercalators, (4) detection via either secondary antibodies, fluorescent DNA stains (or the polymerase chain reaction for especially sensitive detection of the presence of conjugate), (5) the ability to use enzymes to specifically cut and religate the molecule, and (6) the possibility of forming specific hetero-bis dimers.

The other preferred method of the invention for preparing DNA-antibody, etc. conjugates involves the synthesis of 5' thiolated complementary single stranded DNAs. Each of the 5'-thiolated single-stranded DNAs is synthesized by standard β-cyanoethylphosphoramidite chemistry. A sulfhydryl group, protected by a trityl group, is introduced into the 5'-terminus of a single-stranded DNA molecule in the final step of automated DNA synthesis. The synthesized single-stranded DNA is purified by ion exchange chromatography. The purified single-stranded DNA is dissolved in 0.1M triethylammonium acetate (pH 6.5). To this solution, 0.15 volumes of 1M silver nitrate are added, and the mixture is allowed to stand at room temperature for 30 min. To remove the silver, 0.3 volumes of 1M dithiothreitol are added, and the mixture is allowed to stand at room temperature for 30 min, followed by centrifugation. The precipitate is washed with an equal volume of 0.1M triethylammonium acetate (pH 6.5). Released trityl groups are observed as an orange color in the precipitate. Excess dithiothreitol is removed by ethanol precipitation.

The complementary thiolated DNAs a referred to as DNA-A and DNA-B. The DNAs can be prepared so that after annealing, the resulting double-stranded DNA contains a sequence which can be cleaved by a restriction endonuclease.

Thionitrobenzolate (TNB) derivatized antibodies or antibody fragments are also prepared. As with the biotin/streptavidin conjugations almost any antibody and Fab' antibody fragment including but not exclusive of fragments such as IgG1, IgG2a and IgG2b can be used to form the conjugate. However, Fab' antibody fragments are preferred.

The antibody molecule can be described as consisting of 3 portions, namely the Fc and 2 Fab domains, linked together by disulfide bonds to form the whole immunoglobulin. By treatment with the proteolytic enzyme pepsin, the Fc portion may be cleaved away from the remaining $(Fab')_2$ fragment. Each binding site of this bivalent fragment is in close proximity to the other, with their relative positions limited only by the disulfide bridges that remain to connect the two monovalent Fab fragments (Nisonoff et al., 1975). Furthermore, single Fab fragments may be generated by cleavage with the proteolytic enzyme papain. Papain, however, removes the thiol groups and is not appropriate for derivatization by thiolation.

The $F(ab')_2$ fragments of the invention may be prepared from antibodies such as IgG1, IgG2a and IgG2b by a standard pepsin digestion method. The $F(ab')_2$ fragment or antibody is incubated at room temperature overnight in 2 mM 2-mercaptoethylamine.HCl dissolved in 0.1M sodium phosphate (pH 6.8)-1 mM EDTA to reduce disulfide bonds between its heavy chains. Excess amounts of solid Ellman's reagent [5,5'-dithiobis(2-nitrobenzoic acid] are added into the solution and dissolved. The mixture is incubated at 25° C. for 3 hr. to allow the Ellman reagent to react with the sulfhydryl groups of the antibody or Fab' fragment, resulting in the formation of thionitrobenzoate-derivatized Fab' (TNB-Fab') or TNB derivatized antibody. Unreacted Ellman's reagent is removed by gel filtration.

This preparation results in two TNB-Fab' fragments, referred to as TNB-Fab'-1 and TNB-Fab'-2 or two TNB antibodies referred to as TNB-Aby-1 and TNB-Aby-2. Fab'-1 and Fab'-2 or Aby-1 and Aby-2 bind antigen-1 (Ag-1) and antigen-2 (Ag-2), respectively. If the conjugate is to result in bispecific antibodies, then of course Ag-1 and Ag-2 will be different and the fragments or antibodies that bind to them will also have different antigen specificities with respect to each other.

5'-thiolated single-stranded DNA is mixed with an equimolar amount of TNB-Fab' or TNB-Aby to allow the sulfhydryl group of the single-stranded DNA to exchange the TNB group of the Fab' or Aby, resulting in the formation of a disulfide bond between the single-stranded DNA and the Fab' or Aby. The reaction can be monitored by the release of TNB, which has a yellow color with an absorption maximum at 412 nm. The resulting single-stranded DNA-Fab' or DNA-Aby conjugate is purified by anion exchange chromatography.

By using this method, DNA-A and -B are conjugated to Fab'-1 and Fab'-2 or to Aby-1 and Aby-2, respectively.

Equimolar amounts of two single-stranded DNA-Fab' conjugates or DNA-Aby conjugates, i.e., a DNA-A +Fab'-1 conjugate and a DNA-B+Fab'-2 conjugate or a DNA-A+ Aby-1 conjugate and a DNA-B+Aby-2 conjugate, are mixed, and the two single-stranded DNA are allowed to anneal by slowly lowering the temperature. The resulting conjugate if bi-specific (i.e., bis(Fab')-DNA conjugate or bis(Aby)-DNA) contains two different Fab' molecules (Fab'-1 and Fab'-2) or antibody molecules (Aby-1 and Aby-2) cross-linked by a double-stranded linker DNA composed of DNA-A and DNA-B. Because each Fab' fragment or antibody is attached at the 5'-terminus of a single-stranded DNA, the two Fab' fragments are located at the termini of the double-stranded linker DNA molecule.

In the course of the invention, nuclease cleavage and religation of the bis-antibody DNA conjugates can be incorporated into their use as well as cleavage with DNAse I. DNAse I is a DNA-specific but nonsequence-specific endonuclease that degrades double-stranded DNA to its constituent nucleotides. One of the great virtues of using DNA as a linker between 2 protein molecules is that a wide variety of different enzymes can be used to probe or change the nature of the linker. All of this can be done with the sensitivity of PCR and its sequence specificity to judge the nature of the religation products when more than one type of epitope is present. These experiments are feasible even at the level of single cells, and under physiological conditions even in rather complex biological preparations. Although similar information may be obtained using the technique of fluorescence photobleaching and recovery, in situations where low numbers of epitopes are involved, i.e., below the optical detection limit, this technique should prove advantageous. DNA biospecific antibody conjugates of the type described above can also be used to measure the mobility of particular epitopes, and whether they can cross into domains where other epitopes are present. The use of thiol groups in the antibody Fab' fragment hinge region allows for well localized sites of cross-linking, as their positions are fixed relative to the antigen combining site (for example, see Green, 1969). The well defined structure of the resulting bispecific antigen binding molecule can thus be easily changed to meet the requirements of various applications by simply changing the structure of the intervening double-stranded DNA' molecule. In addition, because only thiol groups of the antibodies are reacted in formation of the bispecific molecule, readily reactive free lysine groups still remain and may be dye-labeled, simplifying detection of the bispecific antibody.

When using such bispecific antibody constructs, as described above, against cellular targets, care must be taken to avoid problems resulting from the ever-present danger of extracellular nucleases and also from the presence of DNA receptors on a variety of cell types. In the case of both human malignant and normal peripheral blood lymphocytes, this caveat is quite serious as both an 80 kDa receptor for small oligonucleotides (Loke et al., 1989) and a 30 kDa receptor for larger DNAs (Bennett et al., 1985) have been isolated. Both of these receptors have been found to be mutually exclusive in their binding preferences. It is estimated that, on human peripheral blood lymphocytes, the dissociation constant for the 30 kDa receptor is approximately $10^{-9}$M and these receptors are present in a quantity of greater than $5\times10^4$ per cell (Bennett et al., 1985). In the case of the 80 kDa receptor, it is estimated that on fibroblasts the dissociation constant is approximately $2\times10^7$M and these receptors are present in a quantity of roughly $1.2\times10^5$ per cell (Yalubov et al., 1989). It is of note that both of these receptors exist in large abundance on the cell surface, and that their affinities for DNAs rival, within a few orders of magnitude, those of some Fab antibody fragments for their cell surface targets. Furthermore, both receptors have also been shown to display receptor mediated endocytosis of DNAs, accompanied in some cases by known second messenger signaling events (Bennett et al., 1985; Loke et al., 1989; Yakubov et al., 1989). Thus even if carrier DNAs are added to the reaction mixtures when probing physiological events on cells, it is very difficult to control or even fully account for possible induced second messenger and other DNA receptor triggered processes, as they have not yet been fully elucidated. As in the GA2 experiments described in Example 2, the presence of DNA receptors on lymphocytes and other cell types may be prohibitive to practical application of low affinity DNA cross-linked antibodies to cellular physiological studies.

For intermediate and higher affinity constructs, a plethora of applications exists. In particular, as shown in Example 3, the hetero-bispecific conjugates of this invention are used to investigate the function of cell surface molecules and their relationship to each other. Further, the bispecific antibodies made according to the methods of the invention can be used in exactly the same manner as other bispecific antibodies.

The methods described here are useful in defining and manipulating other multi-receptor complexes. A number of other T cell surface components have recently been found to co-aggregate with the TCR. Specifically, TCR has been co-immunoprecipitated with the following: CD8 (Gallagher et al., 1989); CD45 (Ledbetter et al., 1988; Volarevic et al., 1990; Mittler et al., 1991) although no energy transfer could be detected between CD3 and CD45 on a CD4 transfected T cell hybridoma (Mittler et al., 1989) or on resting human peripheral blood T cells, energy transfer was seen on activated human T lymphocytes (Mittler et al., 1991); fyn (Samelson et al., 1990); $p56^{lck}$ (Veillette et al., 1988; Burgess et al., 1991); a 32-kD GTP-binding protein which co-precipitates with both CDT and $CD8\text{-}p56^{lck}$ T cell receptor complexes (Telfher and Rudd, 1991); and, most recently, CD2 and CD5 which have been co-immunoprecipitated with CD4, CD8 and TCR on normal rat T cells (Beyers et al., 1992). The DNA conjugates of the invention can be applied to the study of these other components of the putative TCR-associated multi-molecular complex.

The present invention is described in detail by referring to the Examples below.

EXAMPLE 1

Preparation of Bis-(Streptavidin-Antibody) Double Stranded DNA Conjugates

Materials and Methods

Synthesis of biotinylated DNA

The complementary 32 base oligonucleotides (SEQ ID NOS:1 and 2) were synthesized using standard automated cyanoethyl phosphoramidite chemistry on the 1 µmole scale (Applied Biosystems, Foster City, Calif.). Biotin groups were incorporated 5' via a biotin phosphoramidite (Midland Certified Reagent Co., and Operon Technologies, Inc.) at the last step in automated synthesis. The crude products were then desalted, dried, and resuspended in buffer containing 10 mM Tris.Cl/1 mM EDTA/130 mM NaCl pH 7.2 (STE) at a concentration of 100 $A_{260}$ units/ml and used without further purification.

Conjugation of DNA to Streptavidin

In separate reaction vessels, each complementary strand of the 32mer (SEQ ID NOS:1 and 2) was reacted with 1 mg of either unlabeled, or fluorescein isothiocyanate (FITC)- or tetramethylrhodamine isothiocyanate (TRITC)-labeled streptavidin (Pierce Chemical Co.) in 1 ml of STE buffer, with the crude oligonucleotide in 2-fold molar excess. Conjugation reactions were carried out for 1 to 14 hours at 4° C. in the dark.

Purification of DNA-Streptavidin Conjugates

The resulting mixtures were passed over 1 ml 2-iminobiotin streptavidin affinity columns (Calbiochem) in 50 mM sodium carbonate and 1M NaCl at pH 11. After washing with 10 ml of buffer, unconjugated streptavidin and unsaturated, DNA-conjugated streptavidin were then eluted with 10 ml of 50 mM ammonium acetate, 0.5M NaCl and 6M urea at pH 4, and 2 ml fractions were collected. These fractions were then concentrated and exchanged into STE buffer using 10,000 molecular weight cut-off ultrafiltration membrane units (Amicon). The individual reaction mixtures were further purified over a 7.5×300 mm 300,000 molecular weight exclusion gel filtration HPLC column (TSK3000SW, Beckman) flowing at 1.5 ml/min. Monitoring absorbance at 230 and 254 nm, fractions corresponding to unconjugated, singly-conjugated, and more highly conjugated streptavidin were manually collected. Colored conjugates were also monitored at 490 and 550 nm.

Effect of NaCl Concentration on Conjugate Gel Filtration

In gel filtration buffer containing 20 mM Tris-Cl and 2 mM EDTA, the NaCl concentration was varied from 0 to 500 mM in an attempt to uncover any complicating ionic interaction in the gel filtration separation system. Conjugation reaction products were then analyzed as described above.

Synthesis of Double-Stranded DNA-Protein Conjugates

After isolation of DNA strands singly-conjugated with streptavidin, each complementary conjugate was reacted with excess amounts of biotinylated goat-anti-human IgG (Organon-Teknika) in STE buffer. The antibody fragment-saturated complementary conjugates were then mixed and allowed to anneal overnight in the dark at 4° C. Alternatively, single-stranded conjugates that had not been reacted with biotinylated antibody were also annealed. The resulting double-stranded conjugates were then purified using a 7.5×300 mm 1,000,000 molecular weight size exclusion column (TSK4000, Toso Haas) under the same conditions described above, except using 630 mM instead of 130 mM NaCl. Note that the resulting molecules are expected to contain protein moieties that will be situated approximately on the same face of the DNA double helix.

The complete synthetic scheme is diagrammed in FIG. 1.

Gel Retardation Assay

Four percent agarose minigels were run in 90 mM Tris-borate, 2 mM EDTA and 1 $\mu$g/ml ethidium bromide at pH 8.3. This corresponds to standard DNA electrophoresis conditions. After viewing DNA locations by ultraviolet excitation, gels were dried and stained for protein with Coomassie Brilliant Blue R.

Electron Microscopy

Transmission electron microscopy at 80 kilovolts was carried out on uranyl acetate negatively-stained samples. The staining method was a variation of that used by Green (1969). The protein-containing samples were suspended in STE buffer at approximately 50–100 $\mu$g/ml. One $\mu$l of sample solution was then applied to a carbon coated 400-mesh copper grid. Excess solution was then absorbed off with filter paper. 1.5% uranyl acetate negative stain was applied before microscopy.

Results

Synthesis of DNA-Streptavidin Conjugates

The synthesis is outlined in FIG. 1. Streptavidin was reacted with 2-fold molar excess of crude biotinylated single-stranded 32 base long oligonucleotide (SEQ ID NO:1). Likewise, the reaction with the complementary oligonucleotide sequence (SEQ ID NO:2) was carried out. Syntheses with FITC- and TRITC-streptavidin were also done. Initial purification of product from reactants was performed by open column reversible affinity capture on 2-iminobiotin. Subsequently, purified material was again fractionated by gel filtration HPLC with real time multi-wavelength absorbance monitoring at 230, 254, 490 and 550 nm.

Theoretically these reactions should produce a statistical distribution with streptavidin bound to 1 to 2 DNAs as the major product, depending on the purity of the biotinylated DNA solution which was usually 70–90%. However in all reactions, as will be shown below, on average less than 1 DNA bound each streptavidin. Possible explanations include: heterogeneous biotinylation of DNA with only a subset, for unknown reasons, able to bind streptavidin; steric hindrance caused by the DNA moiety; local charge repulsion also caused by the DNA; and competition with 2-iminobiotin which normally has much lower affinity for streptavidin than biotin. Purified conjugates were then either directly annealed to form the double-stranded conjugate or pre-saturated with biotinylated antibody before annealing.

Structure of Cross-Linking DNA Sequences

The end-biotinylated 32 base pair sequence (SEQ ID NOS:1 and 2) is shown in FIG. 2. Using Tinoco energy rules (Williams and Tinoco, 1986), each complementary single strand contains only –0.60 kcal of folding energy. Using the program of Olson and Srinivasan (Olson and Srinivasan, 1988), the double-stranded structure may be considered a rigid rod, as expected for such a short piece of double-stranded DNA (data not shown). Curiously, by capillary gel electrophoresis, the 2 complementary biotinylated single strands eluted quite differently (data not shown). This difference cannot be explained by minimal differences in structure or nucleotide composition.

Purification of Single-Stranded and Double-Stranded DNA-Streptavidin Conjugates In FIGS. 3(A) and 3(B) are shown HPLC gel filtration traces of the complementary single-stranded DNA-streptavidin conjugates (SEQ ID NOS:1 and 2) after separation from free DNA and saturated conjugates using reversible affinity chromatography with 2-iminobiotin. After separation of the conjugation mixture into 3 fractions or peaks as shown in FIGS. 3A and 3B, the ratios of absorbencies at 260 (FIG. 3A, solid line) and 280 (FIG. 3B, dotted line) nm were approximately as follows: 1.4 (peak 1), 1.3 (peak 2) and 0.9 (peak 3). The experimentally determined ratio for unconjugated streptavidin was found to be 0.5, and that for a 1:1 molar mix of DNA and streptavidin was 1.3. Thus each conjugation based on these absorbance ratios, could be divided into 3 populations: unconjugated (part of peak 3), streptavidin conjugated with a single DNA (all of peak 2 and part of peaks 1 and 3), and streptavidin conjugated with more than 1 biotinylated DNA (part of peak 1). Fraction 2, containing the desired species, is the purest. However, fraction 3 appears to be significantly contaminated by DNA-containing streptavidin. It can be observed that one strand formed conjugates more readily than the other. That same strand was also found to run much faster than the other by capillary gel electrophoresis (data not shown). Although it was assumed that streptavidin-biotin binding occurred, the possibility that streptavidin may simply be caging with the DNAs cannot be discounted. The identical peaks of the 2 complementary reactions were then mixed in equal volume and reacted overnight at 4° C. The next day they were analyzed by gel filtration. The resulting traces are shown in FIG. 3C (mixture of peaks 1 in FIGS. 3A and 3B), FIG. 3D (mixture of peaks 2 in FIGS. 3A and 3B) and FIG. 3E mixture of peaks 3 in FIGS. 3A and 3B). In FIG. 3C, the first peak (indicated by an arrow) after the void volume most likely corresponds to impure double-stranded conjugate, while the 2 other peaks can be assigned to unconjugated and singly conjugated streptavidin. In FIG. 3D, which represents a near equimolar mixture of peak 2 conjugates, a major double-stranded conjugate peak is seen with a small unannealed lagging peak also present. Note that the double-stranded peaks in FIGS. 3C and 3D elute at approximately the same time, supporting the hypothesis that they present the same bis-streptavidin double-stranded DNA conjugate species. In FIG. 3E 2 major peaks are evident, corresponding to unconjugated and contaminating single oligonucleotide-conjugated streptavidin.

To confirm that minimal or no free DNA contaminated any of the collected peaks, the following was noted: in control runs of both single and double-stranded 32mer (SEQ ID NOS:1 and 2) on the gel filtration column, all DNAs were found to elute at much later times than any of the collected peaks; the ultraviolet spectrum of all collected fractions contained peak absorbencies characteristic of streptavidin at 210 nm, corresponding to absorption by peptide bonds and certain amino acid residues, and 290 nm, corresponding to absorption by tyrosine residues. In the case of the double-stranded DNA conjugate, the ratio of absorbencies at 260 and 280 nm was found to be the same as that of the single-stranded conjugates, further supporting the contention that no unconjugated oligonucleotides participated in the annealing reaction.

To confirm synthesis of the double-stranded DNA-bis-protein conjugate, the annealing reaction was repeated using FITC- and TRITC-streptavidin separately conjugated to different complementary single strands. The single-stranded conjugated and unconjugated colored streptavidins did not separate as well as the uncolored streptavidin conjugation reactions. In fact, they very nearly coeluted at the same position as unconjugated uncolored streptavidin (data not shown). However, upon annealing the crude reaction products, bi-colored double-stranded conjugates were detected. A resultant HPLC gel filtration trace with absorbencies monitored at 230 and 254, and (B) 492 and 550 nm identified a (FITC-streptavidin)-double stranded DNA-(streptavidin-TRITC) conjugate. As expected, bis-streptavidin-double-stranded DNA (i.e., hetero-bis conjugate) was identified to absorb quite well at all of these wavelengths (data not shown).

However, 2 bis-conjugate peaks were apparent at 230 and 254 nm (data not shown). One likely explanation is the presence of significant amounts of multiply DNA-conjugated streptavidin which may anneal to form tris- and higher order conjugates. Another explanation is that dye-labeling causes heterogeneity in streptavidin that becomes apparent by gel filtration after binding of biotinylated DNA. These possibilities remain to be confirmed.

Restriction Enzyme Digestion of Bis-Streptavidin Double-Stranded DNA in Conjugate The 32mer sequence (SEQ ID NOS:1 and 2) was designed to contain a Sal I restriction enzyme site in the middle. Sal I was selected because it has maximal activity under physiological conditions without the need for reducing agents. However, when treated with Sal I, the conjugate is either cut very little, or not at all (data not shown). In comparison, the unconjugated 32mer (SEQ ID NOS:1 and 2) was easily digested by Sal I. This was because the proper digestion conditions were not determined. Longer DNA strands such as those of about 50–60 base pairs or greater will provide the proper conditions for cleavage by a sequence specific restriction enzyme. The conjugate was, however, sensitive to DNAse I (data not shown).

Effect of NaCl Concentration on Separation of Conjugated and Unconjugated Streptavidin by Gel Filtration Because the DNA-conjugated streptavidin separated from unconjugated streptavidin much better than would be expected from molecular weight and shape considerations, the possibility of the occurrence of ionic interactions with the gel filtration column were explored. Other workers have shown that DNA experiences repulsive interactions with certain gel filtration matrices (Ellegren and Laas, 1989). Thus DNA-conjugated streptavidin may elute much faster by gel filtration than predicted from molecular weight considerations alone. The fact that DNA is non-globular may also aid this separation.

To determine the extent of ionic interaction between DNA and our gel filtration matrix, separations with increasing concentrations of NaCl were carried out. In doing so, the NaCl concentration required for optimal separation were determined. FIGS. 4A through 4F demonstrate the effect of increasing NaCl concentration on the elution of one oligonucleotide-streptavidin conjugate. Surprisingly, in FIG. 4A at 50 mM NaCl two conjugate peaks were seen in addition to the later eluting unconjugated peak. In FIG. 4B at 100 mM NaCl again two conjugate peaks were evident. However, the ratio of absorbencies at 254 nm of the 2 conjugate peaks changes with the leading peak becoming dominant at 100 mM NaCl. This result is not simply an experimental variation, as it is consistently seen over several trials. The possibility of DNA-matrix interaction versus the possibility of independent DNA salt interaction cannot be easily differentiated here. At 150 mM NaCl in FIG. 4C the doublet conjugate peaks became a singlet, as previously observed. The reason for this doublet to singlet transition cannot be explained at this time. The elution time of this singlet peak corresponds most closely to the leading peak of the lower salt doublet. However, it cannot definitively be stated that they are actually the same species. At 250 mM (FIG. 4D) and 500 mM NaCl (FIG. 4E), the distinct singlet is seen to be retained, although conjugated and unconjugated peak separation appears to decrease slightly. Although the cause of these NaCl induced changes in elution pattern cannot easily be explained, it has been shown that ionic interactions are a very important consideration in such separations. Fortuitously, for preparative chromatography, 150 mM NaCl, which is approximately the physiological salt concentration, appears to provide the best separation of DNA-conjugated and unconjugated streptavidin.

In an attempt to further explain the nature of the low salt DNA-streptavidin doublet, the ultraviolet absorption spectrum of the ensemble doublet seen at 50 mM NaCl was compared to that of the singlet seen at 150 mM NaCl to determine if any component of the doublet is not also found in the singlet peak. FIG. 4F shows the normalized ultraviolet absorption spectra of DNA-streptavidin conjugate peaks at 50 mM (sum of 2 peaks) and 150 mM (single peak) NaCl obtained by diode array detector scans of analytical samples. Taking into account solvent-induced spectral perturbations and effects of spectral normalization, there is no dramatic difference between the spectra from 250 to 320 nm. Below 250 nm, differences seen were most likely due to differences in solution turbidity due to different NaCl concentrations. The same can be said for the unconjugated streptavidin peaks. In addition, when the spectra of the individual peaks of the 50 mM NaCl doublet are compared, there is also no difference ($A_{260}/A_{280}$=1.3 for both). Thus these results do not simply represent resolution of streptavidin with 1 and 2

DNAs attached at low but not high salt concentrations, in which case these 2 species should have displayed different ultraviolet absorption spectra. Furthermore, the high salt singlet peak eluted at the same time as the leading peak of the low salt doublet, suggesting interconversion rather than simple merger of the doublet peaks.

Synthesis of a Bis-(Streptavidin-Antibody)-Double-Stranded DNA Conjugate

The purified single-stranded DNA-streptavidin conjugates (SEQ ID NOS:1 and 2) were separately reacted with excess biotinylated goat anti-human IgG and then allowed to anneal to form the desired bis-(streptavidin-antibody)-double-stranded 32mer (SEQ ID NOS:1 and 2). For the HPLC traces given in FIG. 5, a TSK 4000 SW (1,000,000 molecular weight) size exclusion column in STE buffer flowing at 15 ml/min. was used, with a characteristic 2 peak void from 0 to 3 min under conditions used (see Materials and Methods). FIGS. 5A and 5B give the elution profiles of the single-stranded DNA-streptavidin conjugates. FIG. 5C shows the result of annealing the 2 fractions. FIGS. 5D and 5E display the elution profiles of the biotinylated antibody saturated-single-stranded DNA-streptavidin conjugates. The peak seen at 6.4 min represents free antibody, as determined by the ratio of absorbencies at 260 and 280 nm. The other major peak seen in each trace is the desired conjugate. The double-stranded product, despite efficient annealing as judged by the virtual disappearance of the single-stranded antibody-conjugated peak in the equimolar reaction, could not be easily eluted at 130 mM NaCl (data not shown). FIG. 5F shows the elution profile of the double-stranded conjugate which was achieved by raising the NaCl concentration of the elution buffer to 630 mM. The peak corresponding to the bis-conjugate, indicated by the arrow in the figure, was determined by comparison to runs of the single-stranded antibody conjugates as well as the double-stranded streptavidin conjugate under the same salt conditions (data not shown). Note in FIGS. 5E and 5F, conjugate peaks elute unavoidably close to the void. Identity of peaks was confirmed by real time absorbance spectrophotometry (data not shown).

Alternatively, instead of biotinylated antibody saturation, a single biotinylated antibody can be bound to each streptavidin-single-stranded DNA conjugate before annealing. By gel filtration, such conjugates are found to elute slower than the biotinylated antibody saturated molecule (data not shown), and can thus be simply purified. However, the isolation is more laborious as the single antibody conjugate must be captured as a transient intermediate step to formation of the totally saturated molecule. Another alternative which was explored was saturation with biotinylated F(ab')$_2$ antibody fragments. These conjugates have the advantage of eluting from the gel filtration column under normal salt conditions (data not shown), rather than the high salt conditions required to elute the biotinylated whole antibody saturated conjugates.

The analytical system currently used did not allow quantitation of the total antigen binding valence of the bis-(streptavidin-antibody)-double-stranded DNA molecule. However, it was determined that the putative antibody-containing fractions described above actually contained protein in addition to streptavidin. In comparison to non-antibody-containing conjugates, the ratio of absorbance at 260 and 280 nm, as determined by diode array scan over the corresponding peaks of the antibody containing conjugates, was seen to decrease to 1.2, indicating a higher protein content for these fractions. Moreover, the ratio of absorbance at 210 and 260 nm was seen to increase from 3.4 for the non-antibody containing species to 5.4 for the antibody containing species, further confirming increased protein content. For unconjugated biotinylated antibody, the ratio of absorbance at 260 and 280 nm was found to be 0.6, and the ratio of 210 to 260 nm absorbance was found to be 69.

Gel Retardation Assay

To determine the altered mobility imparted to the 32mer sequence (SEQ ID NOS:1 and 2) by end-linked proteins, gel retardation assays were performed. In FIG. 6, lane 1 was loaded with a 123 base pair ladder, 2 the double-stranded 32mer, 3 the bis-streptavidin-conjugated double-stranded 32mer (SEQ ID NOS:1 and 2), 4 the bis-(streptavidin-antibody)-conjugated-double-stranded 32mer (SEQ ID NOS:1 and 2), and 5 and 6 the streptavidin-antibody-conjugated single-stranded 32mers (SEQ ID NOS:1 and 2). Run using a 4% agarose gel in TBE, pH 8.3 and $\mu$g/ml ethiduim bromide (standard DNA electrophoretic conditions), the resulting ultraviolet excitation of the ethidium bromide stained gel is shown in FIG. 6. It can be observed that the bis-streptavidin-double-stranded 32mer (SEQ ID NOS:1 and 2) in lane 3 displays a substantially retarded band when compared to non-conjugated 32mer (SEQ ID NOS:1 and 2) in lane 2. Furthermore, bis-(streptavidin-antibody)-double-stranded 32mer (SEQ ID NOS:1 and 2) in lane 4 did not even enter the gel. Lanes 5 and 6 gave no detectable signal, as only single-stranded DNA was present. Upon Coomassie staining for protein (data not shown), a band corresponding to free antibody was seen in lanes 4, 5 and 6 as expected (in reference to the 123 base pair ladder in lane 1, antibody was seen at 861 base pairs, i.e., step 7). Protein was also seen at the edge of the well of lane 4 as expected. Streptavidin, which stains weakly with Coomassie Brilliant Blue R, could be seen faintly in lanes 3, 5 and 6 at the same position as the retarded band in the ethidium bromide stain of lane 3 (data not shown). The failure of bis-(streptavidin-antibody)-double-stranded 32mer (SEQ ID NOS:1 and 2) to enter the gel may prove useful for purification purposes. Of note, though, is the fact that bis-(streptavidin-F(ab')$_2$ antibody fragments)-double-stranded 32mer (SEQ ID NOS:1 and 2) entered the gel under these same conditions (data not shown).

Electron Microscopy

A uranyl acetate negatively-stained electron micrograph of the bis-(streptavidin-antibody)-double-stranded 32mer (SEQ ID NOS:1 and 2), shown in FIG. 7, revealed two radially striated globular molecules connected by a 150–200 Å bridging structure. From previous electron microscopic studies, it was determined that the dimensions of the antibody molecule are approximately 120×120×110 Å (Green, 1969). Thus the globular molecules, thought to contain streptavidin and more than one antibody, at the ends of the 32mer (SEQ ID NOS:1 and 2) appeared smaller than expected. However, such an observation is based on the limitation of the two-dimensional microscopic view, as well as the possibility that the protein ends may have collapsed under the electron microscopic conditions used. Also seen in the same microscopic preparation were a few unconnected globules with and without bridge-like structures projecting from them (not shown). Attempts at depositing the non-antibody containing molecule as well as free DNA on grids were unsuccessful.

In previous work studying the relationship between TCR and CD4, singlet-singlet energy transfer was used (Chuck et al., 1990). However, experiments using double-stranded DNA as the long range cross-linker, will enable investigators to address whether the TCR must be closely associated with CD4, or simply be triggered synchronously with the CD4 molecule.

EXAMPLE 2

Separation of Semisynthetic Bispecific Antibodies by Annealing Complementary Oligonucleotide-Immunoglobulin G Fab' Fragment Conjugates The use of 5' end-thiolated single-stranded DNA as a cross-linking agent and subsequent double-stranded DNA formation via a simple annealing reaction presents a novel method to control the 3-dimensional spatial separation at the combining sites in bispecific antibodies and to produce a resultant molecule of highly defined structure. This example describes the use of a well characterized and easily synthesized DNA molecule as an antibody Fab' fragment hinge cross-linker.

Materials and Methods

Antibodies

Affinity-purified polyclonal goat antihuman IgG was purchased (Sigma Chemical Co.). Purified mouse anti-human CD4 antibody anti-Leu3a (IgG1) was a gift from E. Engleman. Mouse anti-human MHC I antibody GA2 (IgG1) and mouse anti-human TCR idiotype T40/25 (IgG2a) were produced as ascites in Balb/c mice. All ascites were used after single saturated ammonium sulfate precipitations. FITC-anti-Leu3a was purchased (Becton-Dickinson) and TRITC-T40/25 and FITC-labeled goat anti-mouse IgG were labeled as previously described in Chuck et al., 1990.

Cells

The human T cell leukemia cell line, HPB-ALL, was maintained in Iscove's modified Dulbecco's medium supplemented with 10% fetal calf serum and appropriate antibiotics and fungicide as set forth in Chuck et al., supra. Both TCR positive and negative clones were used.

Cross-Linking DNA Sequence

A synthetic 32mer (SEQ ID NOS:1 and 2) was designed and prepared as described in Example 1.

Preparation of 5'-Thiol Modified Oligonucleotides

Trityl protected thiol groups were introduced in the final step of automated DNA syntheses using standard β-cyanoethyl phosphoramidite chemistry on the 1 μmol scale (Operon Technologies, Inc.). After normal ammonium hydroxide deprotection, further purification was occasionally carried out by MonoQ anion exchange FPLC (Pharmacia). However, this purification step was found to be unnecessary in most cases. The products were then evaporated to dryness. Detritylation was performed essentially according to the method of Connolly and Rider (1985). The dried oligonucleotides were resuspended in 0.1M triethylammonium acetate pH 6.5 (TEAA) at concentrations of approximately 100 $A_{260}$ units per ml. The TEAA buffer was prepared by titrating a 1.7% solution of HPLC grade triethylamine with glacial acetic acid to pH 6.5. The solution was then diluted to 0.1M by addition of distilled deionized water until a 1.4% triethylamine solution was obtained. Next 0.15 volumes of 1M silver nitrate were added to each oligonucleotide-containing solution and left to react at room temperature for 30 min. To remove the silver, 0.30 volumes of 1M dithiothreitol were added and the mixture was left to stand at room temperature for 30 min. This large amount of dithiothreitol is needed to effectively remove non-specifically bound silver from the long synthetic oligonucleotide. The suspensions were then centrifuged to remove the precipitated silver dithiothreitol complex. The precipitates were then washed more with 1 volume of 0.1M TEAA. Released trityl groups were observed as an orange color in the precipitate. Excess dithiothreitol was removed by ethanol precipitation.

Successful thiolation was checked by reaction with Ellman's reagent (Pierce Chemical Co.). The thiolated oligonucleotides may be stored as the thionitrobenzyl derivative achieved upon reaction with Ellman's reagent.

Preparation of the Thionitrobenzoate (TNB) Derivative of Antibody Fab' Fragments of Immoglobulin G Activated thiol derivatives were prepared essentially according to the method of Brennan et al. (1985). $F(ab')_2$ fragments, obtained by pepsin cleavage (Parham, 1983) of 1 to 5 mg of polyclonal affinity-purified goat anti-mouse IgG (1 mg), monoclonal mouse IgG1 anti-human MHC class I (GA2) (3 mg) or anti-human CD4 (anti-Leu3a) (4 mg) were incubated overnight at room temperature in buffer containing 0.1M sodium phosphate pH 6.8,2 mM 2-mercaptoethylamine-HCl (Pierce Chemical Co.) and 1 mM EDTA with or without 10 mM sodium arsenite (for free thiol group protection) at a protein concentration of 3 mg/ml. The next day, excess solid 5'dithiobis(2-nitrobenzoic acid) (Ellman's reagent) was added to the solutions to a concentration of 10 mM. After incubation for 3 h at 25° C., the reaction solutions were desalted and exchanged into buffer containing 0.1M sodium phosphate pH 6.8 and 1 mM EDTA using 6,000 molecular weight exclusion polyacrylamide columns. Five mg of mouse IgG2a $F(ab')_2$ anti-human TCR idiotype (T40/25) on HPB-ALL cells, was reduced to Fab' at 37° C. by treatment for 90 min with 1 ml of 50 mM 2-mercaptoethylamine.HCl, 5 mM EDTA, pH 6.0 (according to the manufacturer's instructions, Pierce Chemical Co.). The sample was then desalted, reacted with Ellman's reagent (added as a solid to 10 mM) for 3 hr. at 25° C., and then desalted again into 0.1M sodium phosphate pH 6.8 and 1 mM EDTA as above. In addition, some derivatives were synthesized using FITC- and TRITC-conjugated $F(ab')_2$ as the starting material. The dye molecules were usually attached via ε-amino groups of free lysine residues, and thus would not interfere with these disulfide exchange reactions.

As noted by Jung et al. (1991), TNB-Fab' conjugates may also be formed from $F(ab')_2$ in a single step upon treatment of $F(ab')_2$ with a mixture of reduced and unreduced Ellman's reagent. Thus Ellman's reagent can serve as both reducing and modifying agents, eliminating one chemical step. Although this method is clearly advantageous, at the time of the present studies, the Jung method was not well known and thus was not used. However, it is recommended for future syntheses.

Preparation of Semisynthetic Bispecific Antibodies

Purified, complementary 5'-end-thiolated oligonucleotides (SEQ ID NOS:1 and 2) were separately mixed with equimolar amounts of thionitrobenzoate-derivatized antibody fragments and allowed to react separately for 16 h at room temperature. If crude derivatized oligonucleotide (purity varied from 70 to 90%) was used, the reaction was carried out in two-fold molar DNA excess. The concentration of Fab' in the reaction solution was approximately 1 to 2 mg/ml. Released thionitro-benzoate, as a consequence of disulfide exchange, could be monitored by absorbance at 412 nm ($\epsilon_{412}$=1.36×10$^4$ cm$^{-1}$·M$^{-1}$) and observed as a yellow color in the reaction solution. The reaction mixtures were then exchanged into 20 mM TrisCl and 1 mM EDTA and purified by anion exchange HPLC (7.5 cm×7.5 mm DEAE-3SW, Toso Haas) at a flow rate of 1 ml/min with elution by a 0–800 mM NaCl gradient. Fractions were analyzed with 7.5% SDS-PAGE (Laemmli, 1970) and silver staining (Biorad). Purified Fab'-single-stranded DNA conjugates were then mixed and allowed to anneal at 0° C. SDS-PAGE gels were also stained with ethidium bromide (unfixed) and Coomassie (fixed) stains. To confirm the presence of DNA in putative conjugate fractions, treatments with DNHAse I (Sigma Chemical Co.) were performed. Non-denaturing PAGE analysis (Davis, 1964) was also performed on single and double-stranded conjugates. The entire synthetic scheme is diagrammed in FIG. 8. Dye labeling, which is not illustrated here, may in many cases only be done after Fab'-DNA conjugation, as dye labeling introduces significant heterogeneity in both the reaction and the separation (unpublished observations). Dye-labeled antibody preparations must be purified and characterized before carrying out such conjugation reactions.

Cell Binding Assays

Non-saturating amounts of purified GA2 Fab' single and double-stranded conjugates (20 μl of 10 μg/ml solution) were bound to the surface of 2×10$^5$ HPB-ALL cells at 0° C. for 30 min. After washing with 1 ml of Hanks' balanced salt solution supplemented with 5% fetal calf serum and 0.1% sodium NaN$_3$, cells were secondarily stained with FITC-labeled polyclonal goat anti-mouse antibody again at 0° C. for 30 min. After washing with and resuspending in supplemented Hanks' buffer, samples were analyzed with a FACS 440 (Becton-Dickinson) fluorescence activated cell sorter as previously described in Chuck et al., 1990. Experiments with anti-Leu3a and T40/25 Fab' conjugates were performed under saturating conditions (20 μl of 50 μg/ml solution per 2×10$^5$ cells). In oligonucleotide competition assays, a 50 times molar excess of free oligonucleotide was used. In dye-labeled native antibody blocking assays, cells were treated at 0° C. for 15 min with oligonucleotide-conjugated Fab' fragments before the dye-labeled antibodies were added for another 15 min.

Alternatively, conjugates were 3'-labeled with a single α-$^{32}$P-labeled dideoxy ATP (6000 Ci/mmol, Amersham) by using terminal transferase, desalted and then applied to cells either in single or double-stranded form. One must be aware that terminal transferase and radioactive dideoxynucleotide stock solutions often contain significant amounts of the reducing agent mercaptoethanol. Upon labeling of conjugates, some free DNA will be released and must be accounted for in further analyses. To prevent significant formation of other disulfide exchange products, the final solution may be treated with iodoacetamide to block remaining free thiol groups. Scintillation cocktail (Ready Safe®, Beckman) was added to $^{32}$P-labeled cells before counting.

Dot Blot Assays

A goat anti-mouse IgG Fab'-double-stranded 32mer DNA-streptavidin (SEQ ID NOS:1 and 2) conjugate was synthesized and used to probe mouse IgG immobilized, by dot blot onto nitrocellulose. Synthesis and purification of the streptavidin-single-stranded 32mer DNA (SEQ ID NOS:1 and 2) conjugate was performed as described in Example 1. All manipulations were carried out essentially according to the protocol accompanying the chemiluminescence based non-radioactive detection kit (Biorad) used. FIG. 11 is a pictorial flow chart of the experimental scheme. This method is one that can be used to detect single molecules. In the scheme shown in FIG. 11, the complementary-single stranded DNA that annealed to the immobilized DNA was labeled by the enzyme horseradish peroxidase (HRP). However, in other embodiments of the method, the complementary strand can be labeled with other enzymes, or with an enzyme substrate, a radiolabel or some other appropriate chemical agent. Almost any of the labeling systems used in other assays to detect antigen analytes can be used in this assay. Also in this assay the complementary DNA strand was attached to the label by means of streptavidin/biotin system. Again, in other embodiments of this method, the complementary strand can be attached to the label by means of some other linking group or linking groups.

Results

Cross-Linking of Fab' Antibody Fragments to Complementary Single-Stranded 32mer DNAs by Disulfide Exchange Again synthesis is outlined schematically in FIG. 8. The thionitrobenzoate hinge derivative of 2 separate Fab' antibody fragments, of either the same or different specificity, were mixed and left to react separately with equimolar amounts of either a purified, or 2-fold molar excess of a crude 5' end-thiolated 32 base long oligonucleotide and its thiolated complementary sequence (SEQ ID NOS:1 and 2). The desired Fab'-oligonucleotide product was then separated from remaining unconjugated Fab' fragments and free DNA and recovered by fractionation with HPLC anion exchange chromatography. FIG. 9A shows a Coomassie stained 7.5% SDS-PAGE gel of the crude products of sequential pepsin and 2-mercaptoethylamine.HCl treatment of the anti-MHC I monoclonal antibody, GA2 (IgGl). Of significance is that only mouse antibodies of the IgGl and 2a subclasses can be cleanly digested with pepsin (Parham, 1983). The major product observed in FIG. 9(A) is Fab' (47 kDa). In addition to faint bands corresponding to IgG1 (~160 kDa) and F(ab')$_2$ (~110 kDa), other degradation products are seen, especially below the Fab' band. However, only the Fab' band reacts significantly with thiolated DNA. FIG. 9B shows the ethidium bromide stained unfixed 7.5% gel of SDS-PAGE the crude products of a GA2 Fab'-TNB and thiolated single-stranded 32mer DNA (SEQ ID NOS:1 and 2) disulfide exchange reaction before and after treatment with DNAse I. Indicated with arrows in lanes 1 is GA2 Fab' conjugated to single stranded 32mer (SEQ ID NOS:1 and 2) and in lane 2 GA2 Fab' conjugated to complementary single stranded 32mer (SEQ ID NOS:1 and 2) (i.e., the positions of the separate complementary conjugates) and the original Fab' band. Lanes 3 and 4 of FIG. 9B demonstrate the products after treatment with DNAse I. It can be seen that one conjugate was incompletely degraded to a species with a slower mobility than Fab', while the other was completely degraded to a species with approximately the same mobility as Fab', owing to the differential action of DNAse I on the different complementary strands. That is, DNAse I appeared to digest the B strand more efficiently than the A strand. FIG. 9C is the same gel stained with Coomassie after methanol/ acetic acid fixation. It can be observed that ethidium stains both DNA and protein, with DNA staining much brighter, while the Coomassie stain is specific for protein. The existence of the Fab'-DNA bond was further confirmed with agarose gel retardation assays as described in Example 1, before and after treatment with the reducing agent dithiothreitol or with proteinase K (data not shown).

FIGS. 10A and 10B demonstrate the fractionated products of the 2 complementary single-stranded DNA reactions after separation by anion exchange HPLC using 20 mM Tris.Cl, 1 mM EDTA and 100 to 800 mM NaCl as the running buffer and analysis by silver stained 7.5% SDS-PAGE. The separations were monitored in real time by a diode array absorbance spectrometer coupled directly to a flow cell within the HPLC apparatus. At a flow rate of 1 ml/min, NaCl gradient of 28 mM/min was used. Lanes 1–8 represent 10 µl of each 1 ml fraction eluted with NaCl concentration increased linearly from 576 mM to 800 mM. Lane 9 represents 10 µl of 1 ml fraction eluted with 2M NaCl. In reaction A (thiolated 32mer strand A) (SEQ ID NO:1) of FIG. 10A, the Fab'-single-stranded conjugate, indicated by an arrow, is seen to begin eluting at approximately 604 mM NaCl, while in the complementary reaction B (i.e., complementary thiolated 32mer strand B) (SEQ ID NO:2) shown in FIG. 10B, the conjugate, indicated by an arrow, began eluting at approximately 576 mM NaCl. However, with this particular gradient, free DNA (seen by real time UV absorbance but hidden in the dye front of the silver stained gel) and higher order conjugates eluted soon after. All unconjugated antibody fragments eluted completely by 400 NaCl. Fractions in 10A) lane 2 and 10B) lane 1, both of which are free of unconjugated DNA, were exchanged into 10 mM Tris-Cl, 1 mM EDTA and 150 mM NaCl pH 7.4 and used for further analysis. Protein concentrations were determined with the BCA Protein Assay Reagent® (Pierce Chemical Co.) using conditions insensitive to the presence of DNA. In attempts to circumvent problems associated with purification by anion exchange chromatography, antibody affinity capture with immobilized polyclonal goat anti-mouse IgG was also tried. However, anion exchange provided a much greater yield of stable conjugate than antibody affinity capture (unpublished data).

Conjugate Annealing Reaction

FIG. 10C shows the ethidium bromide-stained 7.5% SDS-PAGE gel of the purified products before and after annealing at 0° C. Lanes 1 and 2 contain the complementary single-stranded conjugates (SEQ ID NOS:1 and 2), and lane 3 shows the product when these 2 samples are mixed in equal volume. As shown and labeled, conjugate A (~70 kDA), in lane 1, was slightly slower than B (~66 kDA), in lane 2, on this particular gel. In estimating the molecular weight, it must be remembered that DNA does not migrate at the same rate as SDS-protein micelles. When mixed, the complementary conjugates anneal to form a bis conjugate which migrates at approximately the same molecular weight as F(ab')$_2$. To ensure that this new species arose as the result of complementary DNA interaction, the sensitivity of this new band to DNAse I was verified (data not shown). FIG. 10D illustrates a silver-stained 7.5% non-denaturing PAGE fractionation of the purified conjugates before and after annealing, with a 123 base pair DNA ladder (lane 1) included for comparison. Lane 4 represents a mixture of Fab'-A (SEQ ID NO:1) and Fab'-B (SEQ ID NO:2) (v/v). As expected, lane 2 (Fab'-A) (SEQ ID NO:1) shows that the A conjugate (SEQ ID NO:1) migrates as a single band. However, as seen in lane 3 (Fab'-B) (SEQ ID NO:2), conjugate B (SEQ ID NO:2) splits into 3 significant bands. Upon annealing, all 3 of these bands are seen to react to form new double-stranded species. A plausible explanation for this behavior is that the reduced Fab' antibody hinge region contains 3 thiol groups which are then reacted to form the activated thionitrobenzoate derivative. Strand A (SEQ ID NO:1) may have preference for only one such thiol, while B (SEQ ID NO:2) may have no preference. Alternatively, A (SEQ ID NO:1) and B (SEQ ID NO:2) may just assume different structural forms upon analysis by non-denaturing PAGE.

Cell Binding of Homo-Bispecific Antibodies

Binding of the GA2 Fab' conjugates, secondarily stained with polyclonal FITC-labeled goat anti-mouse IgG, to the surface of HPB-ALL cells before and after annealing was attempted (see Materials and Methods for experimental details and amounts of reactants used). The hope was that the bivalent antibody would bind much better than the monovalent species, as has been shown for many other antibodies (Parham, 1983). However, although each individual conjugate binds quite well, upon annealing, binding is lost (data not shown). There are two likely explanations: loss of conjugate binding to the cell upon double strand formation, or loss of secondary antibody binding site on the conjugate upon annealing. To differentiate between these two possibilities, the conjugates were labeled with a single 3' α-$^{32}$P-ddATP using terminal transferase. Using these radioactive conjugates, results obtained by fluorescence activated cell sorter (FACS) analysis were confirmed (data not shown). That is, the double-stranded conjugate itself did not bind well to the cell surface. Furthermore, it was also observed that single-strand conjugate cell binding could be competed not only by unconjugated GA2, but also by the unconjugated single-stranded DNA as well as its complementary sequence. Thus there exists a significant oligonucleotide receptor on the surface of HPB-ALL cells. In this case, the affinity of the oligonucleotide rivals closely that of the antibody Fab' for the cell surface. No further experiments were attempted with this set of conjugates.

Dot Blot Assay

To ensure that DNA conjugation does not always interfere with the antibody combining site, as it appeared to do in the GA2 conjugates, we constructed a (polyclonal goat anti-mouse IgG Fab')-(double-stranded 32mer DNA)(SEQ ID NOS:1 and 2)-(streptavidin/biotinylated peroxidase) conjugate, and used it to detect mouse IgG immobilized on nitrocellulose. Submicrogram quantities were detected, confirming that this hetero-bis conjugate was indeed functional (data not shown). The experiment, including the putative conjugate, is described pictorially in FIG. 11.

Although these particular conjugates were not good controls for monoclonal conjugates, as DNA-protein interactions may affect different clones differently, they did suggest effectiveness with the synthesis of the hetero-bispecific DNA-monoclonal antibody conjugate with intact antigen binding ability described below.

Creation and Cell Binding of Hetero-Bispecific Antibodies

All manipulations here carried out as described above except that single-stranded 32mer DNA (A) (SEQ ID NO:1) was conjugated to the mouse anti-human CD4 monoclonal antibody anti-Leu3a (IgG1) Fab', while the complementary strand (B) (SEQ ID NO:2) was conjugated to the mouse anti-TCR idiotype (HPB-ALL) monoclonal antibody T40/25 (IgG2a) Fab' (see *Materials and Methods* for experimental details and amounts of reactants used). FIG. 12A shows the silver-stained 7.5% SDS-PAGE gel of the crude reaction products, before and after DNAse I treatment. Lanes 3 and 4 contain the anti-Leu3a Fab'-A reaction mixture, and lanes 5 and 6 contain the T40/25 Fab'-B reaction mixture before and after DNAse I treatment, respectively. Again, it was observed that the A (SEQ ID NO:1) strand is degraded much less than the B (SEQ ID NO:2) strand conjugate by DNAse I. Lane 1 contains a set of prestained 94, 67 and 43 kDa low molecular weight protein markers (Biorad), and lane 2 contains a 123 base pair DNA ladder (Biorad) for comparison. Because the markers in lane 1 are prestained and run slightly slower than normal, all molecular weights were under estimated.

FIG. 12B is the silver stain of a 7.5% SDS-PAGE gel of the anti-Leu3a Fab'-TNB reaction with thiolated single-stranded 32mer DNA strand (A) (SEQ ID NO:1) after separation by anion exchange HPLC using 20 mM Tris.Cl, 1 mM EDTA pH 7.7 and 500 mM to 800 mM NaCl as the running buffer. At a flow rate of 1 ml/min, a NaCl gradient of 12 mM/min was used. Lanes 1–6 depict 20 μl of each 2 ml fraction eluted with NaCl concentration increased linearly from 548 to 692 mM. The position of Fab'-A conjugate is indicated by an arrow. FIG. 12C is the same as FIG. 12B (SEQ ID NO:2), except that the T40/25 Fab'-TNB and the complementary thiolated 32mer strand (B) (SEQ ID NO:2) were reacted.

It was observed that conjugate A (SEQ ID NO:1) began elution at approximately 596 mM NaCl, while conjugate B (SEQ ID NO:2) began elution at approximately 572 mM NaCl, in agreement with previous results with GA2 Fab'-oligonucleotide conjugates. Yields for all conjugates are 5±1% of crude whole antibody starting material.

To determine the affinities of antibody Fab'-oligonucleotide conjugates relative to the unconjugated parent antibodies, the cell surface antigen binding abilities of the conjugates and the parent antibodies and antibody fragments were determined by subsequent staining with dye-labeled secondary antibody. Shown in Table 1 are the results of experiments testing binding of Fab'-oligonucleotide conjugates to HPB-ALL cells under saturating conditions by secondary staining with FITC-labeled goat anti-mouse IgG. All antibodies and conjugates were used at the same protein concentration, 50 μg/ml. Fluorescence measurements are expressed as the action observed relative to the total signal seen upon double-stranded conjugate cell binding. Comparing staining of T40/25 F(ab')$_2$ with T40/25 Fab'-B, it is apparent that the oligonucleotide conjugate is able to bind to approximately the same extent as the parent F(ab')$_2$. Comparing F(ab')$_2$ to whole T40/25 IgG, fluorescence is decreased by a factor of 0.7, probably due to loss of binding sites in the Fc region. Although we did not stain with anti-Leu3a F(ab')$_2$, using the value obtained by staining with anti-Leu3a IgG and accounting for loss of secondary stain binding sites in the Fc region, it can be predicted that a parent F(ab')$_2$ staining value of 0.7×0.74=0.52, which approximately equals the value of 0.53 obtained by staining with the anti-Leu3a Fab'-A conjugate. Thus anti-Leu3a Fab'-A also retains full binding ability under these conditions. Using a TCR negative clone, T40/25 Fab'-B shows a significant extent (0.17 negative vs. 0.68 positive) of non-specific staining. This non-specificity could not be competed away by free oligonucleotide. In fact, competition with 50-fold molar excess of free over conjugated oligonucleotide, either like or complementary, resulted in insignificant perturbation of all Fab'-oligonucleotide cell binding. However, on a variety of T-ALL CD3 negative clones, using immobilized anti-CD3 stimulation assays, it has been shown that functional CD3:TCR is expressed even when cell surface levels are too low to be easily detected by immunofluorescence techniques such as FACS (Ledbetter et al., 1991). Binding of anti-Leu3a Fab'-A (SEQ ID NO:1) to a CD4 negative clone was not done.

Shown in Table 2 are the results of experiments testing blocking of FITC-anti-Leu3a and TRITC-T40/25 cell binding at 0° C. by the Fab'-oligonucleotide conjugates. Cells were first treated for 15 min with Fab'-oligonucleotide conjugates before addition of dye-labeled antibodies for another 15 min. All fluorescence intensity values are normalized versus values obtained with no conjugate pretreatment. As expected, anti-Leu3a Fab'-A (SEQ ID NO:1) completely blocks FITC-anti-Leu3a binding. Similarly, T40/25 Fab'-B blocks 99% of TRITC-T40/25 binding. However, anti-Leu3a Fab'-A (SEQ ID NO:1) also blocks 11% of T40/25 binding, and T40/25 Fab'-A (SEQ ID NO:1) blocks 65% of anti-Leu3a binding. Assuming that this cross blocking is due to non-specific binding, it is speculated that, at these conjugate concentrations, T40/25 Fab'-B (SEQ ID NO:2) shows a factor of 5.9 more non-specific binding than anti-Leu3a Fab'-A (SEQ ID NO:1). Another possibility is that a large proportion of TCR is complexed with CD4 on HPB-ALL, and that, compared with the unconjugated antibody, the DNA portion of the DNA-T40/25 antibody conjugate extends out far enough to cross-block anti-CD4 binding. The same possibility exists for the DNA-anti-Leu3a antibody conjugate, but that a smaller percentage of T40/25 binding is cross-blocked because TCR is more abundant on the HPB-ALL surface than CD4 (approximately 2:1, unpublished observation). Example 3 below shows that after pre-annealing and forming the AB (SEQ ID NO:1) conjugate at lower concentrations than shown here, both Fab' ends were functional and bound unique saturable receptors.

From Table 1, if it is assumed that the non-specific binding of the single and double-stranded conjugates is the same, then the double stranded conjugate binds less well than theoretically expected (1.00 (AB) (SEQ ID NOS:1 and 2) vs. expected (0.53+0.68=) 1.21 (A (SEQ ID NO:1)+B (SEQ ID NO:2)), or (1.00–1.21)/1.21=17% less well). Possible explanations for this difference include: the double-stranded conjugate experiences significantly less non-specific binding (if it experiences none at all, then we would expect 0.17+$^{0.17}$/5.9=0.20 (17%) less binding, fully accounting for the difference observed), the structure of the double-stranded conjugate restricts binding to only a subset of accessible epitopes due to steric and/or geometrical constraints, or the double-stranded conjugate has a reduced number of secondary antibody binding sites. In any case, this result is completely different than that obtained with the bis-GA2 Fab'-double-stranded 32mer oligonucleotide (SEQ ID NOS:1 and 2) where all binding was lost, albeit under non-saturating conditions.

Discussion

Ever since the elucidation of the double helical structure of DNA, its use as genetic material has been widely observed, utilized and exploited. However, to date, the utility of the DNA molecule as a non-genetic chemical has yet to be fully realized. This Example shows that end-derivatized double-stranded DNA can serve as a cross-linker between different immunoglobulin G Fab' fragments to form a semisynthetic bispecific antibody. Beyond its function as a novel cross-linker, though, DNA possesses a number of potentially very useful properties, including the following: gentle hetero-cross-linking via simple annealing reactions; automated synthesis; controllable sequence variation resulting in well-defined length and structure (useful up to hundreds of base pairs); susceptibility to intercalator incorporation resulting in controllable length, symmetry and stiffness; localized and reversible scission via restriction/religation; and exquisitely sensitive detection via the polymerase chain reaction. However, to enable enzymatic action by restriction enzymes against the intact cross-linking DNA molecule, a somewhat longer DNA sequence (SEQ ID NOS:1 and 2) should be used as the 32mer sequence used here was largely resistant to cleavage by all of the restriction enzymes for which the 32mer oligonucleotide (SEQ ID NOS:1 and 2) has known sites (data not shown). The unconjugated 32mer sequence, (SEQ ID NOS:1 and 2) on the other hand, was susceptible to cleavage by these restriction enzymes, as expected (data not shown). Likely explanations for this behavior are steric hindrance or altered DNA structure. Another difficulty is that reducing conditions are necessary for many DNA modifying enzymes, including ligases and many restriction enzymes. Unfortunately, the model constructs described in this paper all contain easily usable disulfide bond cross-links between protein and DNA. Treatment with reducing agent will destroy these important structural bonds. For applications that require irreversiblity of the protein-DNA cross-link, an irreversible thioether bond may be produced (Glennie et al., 1987).

Semisynthetic bispecific antibodies constructed using 5' derivatized DNA as a cross-linking structure not only allows easy formation of bispecificity via DNA annealing reactions, but also allows controllable 3-dimensional separation of antigen binding moieties through choice of DNA sequence. In most of the previous studies relating to protein interaction, CD4 and TCR were cross-linked by antibodies immobilized on solid supports such as microbeads, where the relative positions of the anti-receptor antibodies were largely unknown. In addition, it was impossible to tell how many receptors were aggregated by the beads at the cell contact point. To answer the receptor association question posed above and avoid the uncertainty of previous studies, cross-linked Fab' fragments of anti-CD4 and anti-TCR over various fixed distances with double-stranded DNA can be used to observe the ability of the bispecific molecules to trigger T cells in comparison to triggering with unlinked antibody fragments. In experiments to be described in Example 3, a prototype bispecific anti-TCR/anti-CD4 antibody-DNA construct was particularly characterized by comparing its binding and effect on CD4:TCR complexes to that of conventional hybrid anti-CD3/anti-CD4 antibodies.

TABLE 1

HPB-ALL cell surface binding of
Fab'-single-stranded 32mer oligonucleotide
(complementary strands A (SEQ ID NO: 1)
and B (SEQ ID NO: 2)) conjugates at 0° C.

|  | Mean relative fluorescence intensity after background correction | |
| --- | --- | --- |
| Conjugate | vs. TCR positive cells | vs. TCR negative cells |
| Pre-annealed AB (SEQ ID NOS: 1 and) | 1.00 | |
| Anti-Leu3a Fab'-A (SEQ ID NO: 1) | 0.53 | |
| T40/25 Fab'-B (SEQ ID NO: 2) | 0.68 | 0.17 |

TABLE 1-continued

HPB-ALL cell surface binding of
Fab'-single-stranded 32mer oligonucleotide
(complementary strands A (SEQ ID NO: 1)
and B (SEQ ID NO: 2)) conjugates at 0° C.

|  | Mean relative fluorescence intensity after background correction | |
| --- | --- | --- |
| Conjugate | vs. TCR positive cells | vs. TCR negative cells |
| Anti-Leu3A IgG | 0.74 | |
| T40/25 IgG | 0.94 | |
| T40/25 F(ab')$_2$ | 0.66 | |

$2 \times 10^5$ cells were treated with 20 μl of the various conjugates at concentrations of 50 μg/ml in the cold for 30 min. After washing twice with Hanks' balanced salt solution, the cells were secondarily labeled with FITC-labeled goat anti-mouse IgG at a concentration of 50 μg/ml. Samples were then washed, resuspended and analyzed by FACS. Fluorescence measurements, after subtracting cellular autofluorescence, are expressed as the fraction observed relative to the total signal seen upon double-stranded conjugate cell binding. Both TCR positive and negative subclone staining are shown for the T40/25 Fab'-B (SEQ ID NO:2) conjugate.

TABLE 2

Blocking of FITC-anti-Leu3a and
TRITC-T40/25 HPB-ALL cell binding
at 0° C. by Fab'-oligonucleotide conjugates

|  | Mean relative fluorescence intensity after background correction | |
| --- | --- | --- |
| Conjugate | Fluorescein fluorescence | Rhodamine fluorescence |
| None | 1.00 | 1.00 |
| Anti-Leu3a Fab'-A (SEQ ID NO: 1) | 0.00 | 0.89 |
| T40/25 Fab'-B (SEQ ID NO: 2) | 0.35 | 0.01 |
| Pre-annealed AB (SEQ ID NOS: 1 AND 2) | 0.00 | 0.00 |

$2 \times 10^5$ cells were treated with 20 μl of Fab'-oligonucleotide (SEQ ID NOS:1 and 2) conjugates at concentrations of 50 μg/ml in the cold for 15 min. Then a mixture of saturating amounts of FITC-anti-Leu3a (10 μl of a 20 μg/ml solution) and TRITC-T40/25 (10 μl of a 50 μg/ml solution) was added for an additional 15 min. Samples were then washed, resuspended and analyzed by FACS. Mean fluorescence intensity values, after background correction, are expressed as fractions relative to total signal seen without pretreatment and competition with Fab'-oligonucleotide conjugates.

EXAMPLE 3

Characterization of Bispecific Anti-CD3/Anti-CD4 Antibody-DNA Constructs

In this example, a bispecific antibody with a variable separation between the anti-CD4 and anti-TCR binding sites was engineered. This semisynthetic bispecific antibody was formed by cross-linking 2 Fab' fragments at the hinge regions with 5' thiolated double-stranded DNA. The resultant molecular geometry could be varied by simply varying the base sequence of the DNA cross-linker. In future work, a panel of these bispecific constructs, each with a different cross-linking DNA sequence, can be used to treat T cells. The effects of these different geometrical constraints on cell triggering can be observed. Here one such construct consisting of anti-TCR (T40/25) Fab' cross-linked to anti-CD4 (anti-Leu3a) Fab' cross-linked by a 32 base pair DNA sequence (SEQ ID NOS:1 and 2) (see Example 2) is characterized.

For comparison, hybrid bispecific antibodies were also engineered in the manner described in Wong, et al. 1989. These bispecific antibodies produced by the hybrid hybridoma method were secreted from cells formed by fusion of two different hybridomas and separated away from the unwanted side products by isoelectric focusing gel electrophoresis (Wong et al., 1989). The final structure of the resultant hetero-bivalent molecule should be very close to that of a native homo-bivalent antibody. In addition, these anti-CD3,4 hybrid bispecific constructs were shown to possess mitogenic capability (Wong, personal communication).

In this example the binding and receptor modulation abilities of the prototypic DNA-cross-linked antibody construct was compared to that of the conventional hybrid anti-CD3/anti-CD4 antibodies. The fluorescence activated cell sorter (FACS) was employed to observe each bispecific species' ability to co-modulate CD4, the TCR, and the CD4:TCR complex as measured by observed change in energy transfer.

Materials and Methods

Cells

The human leukemia T cell line HPB-ALL was propagated in Iscove's modified Dulbecco's medium supplemented with 10% fetal calf serum (FCS), 100 units of penicillin per ml, 100 μg of Fungizone per ml, 50 μg of gentamicin per ml, and 20 mM glutamine. FCS was obtained from HyClone. All other tissue culture reagents were obtained from GIBCO. Only cells in the exponential phase of growth were used in these experiments.

Antibodies and Cross-Linkers

Construction of the anti-Leu3a/anti-T40/25 bispecific DNA cross-linked Fab' fragment construct was described in Example 2. Hybrid hybridoma derived bispecific antibodies were generated by a collaborator, Johnson T. Wong. The anti-CD3 half is derived from parent 12F6, also named CD3,3 (IgG2a), which overlaps the epitopes recognized by OKT3 and Leu4. CD3,4 is a hybrid with OKT4 (IgG2b), and CD3,4B is a hybrid with Jet4B, which cross-blocks both OKT4F and OKT4. CD3,8 is a hybrid with OKT8 (IgG2a). It is interesting to note that that half-antibodies of different subclasses can naturally associate to form these hybrid antibody pairs.

FITC-OKT4 (anti-CD4), FITC-anti-Leu3a (anti-CD4, Becton-Dickinson), TRITC-OKT3 (anti-CD3), and TRITC-T40/25 (anti-TCR idiotype) were used as described in Example 2. Sub-class insensitive FITC-labeled goat anti-mouse IgG (FITC-GαMIgG) was also used. All dye-labeled antibodies were used under saturating conditions.

Binding Curves of Bispecific Constructs

After removing cells from culture, all subsequent manipulations were carried out in ice cold Hanks' balanced salt solution supplemented with 5% fetal calf serum and 0.01% NaN$_3$. Each sample, containing $2 \times 1^5$ cells, was reacted with 25 μl of a different solution containing decreasing amounts of each bispecific construct and the appropriate controls for 30 min at 0° C. After washing, the samples were secondarily stained with saturating amounts of FITC-GαMIgG again for 30 min at 0° C. The samples were then washed, resuspended and analyzed by FACS.

Co-modulation of CD4 and TCR

Two$\times 10^5$ cells per sample were reacted with 25 μl of the appropriate antibody-containing solution for 30 min at 0° C., washed and resuspended in 200 μl of culture medium. Samples were then exposed to either 0° or 37° C. temperature for 30 min. After 30 min, cells were washed with 1 ml of ice cold Hanks' balanced salt solution containing 5% fetal calf serum, 0.01% NaN$_3$ and 10 mM hepes buffer pH 7.4 without phenol red, and restained with saturating amounts of the appropriate cross-blocking dye-conjugated anti-CD4 and anti-TCR antibody pair. Specifically, all anti-Leu3a and/or T40/25 treated samples were stained with a combination of FITC-OKT4 and TRITC-OKT3. All hybrid antibody treated samples were labeled with a combination of FITC-anti-Leu3a and TRITC-T40/25. After 30 min on ice, samples were washed, resuspended, and then analyzed by fluorescence activated cell sorting (FACS) singlet-singlet energy transfer as described below.

Energy Transfer

FITC, TRITC and sensitized TRITC (STRITC) emission of stained cells were measured on a FACS440 (Becton-Dickinson, Mountain View, Calif.) equipped to monitor five parameters using Consort-Vax data acquisition and processing software as described in Chuck et al., 1990.

Dual argon and krypton lasers were used for excitation at 488 nm and 568 nm, respectively. Forward scattered light of 488 nm was collected through a neutral density filter (parameter 1) and light scattered at 90° was collected through a 488/10-nm band pass filter (parameter 4). Emitted light was detected at 90° to the laser beam. FITC fluorescence was excited at 488 nm and collected through a 530/30-nm band pass filter after reflection by a 560-nm dichroic mirror (parameter 2). TRITC fluorescence was excited at 568 nm and collected as a delayed signal through a 630/22-nm band pass filter (parameter 3). Sensitized TRITC (STRITC) emission was excited at 488 nm and collected through a 560 nm dichroic mirror and a 590 nm long pass filter (parameter 5). Thorn EMI model 4001-06-300 photomultiplier tubes were used for measuring fluorescence. There was no detectable spillover of FITC fluorescence into parameter 3 or TRITC spillover into parameter 2. All measurements were collected in list mode. Forward and 90° light scatter were used to select live cells. Cells which scattered light outside of these experimentally determined live cell profiles were considered abnormal or dead and excluded from analysis. This usually represented less than 5% of all cells examined.

The energy transfer efficiency for a single cell can be estimated as:

$$E = [F_{STRITC}(D+A)/F_{FITC}(D+A)] \cdot s \cdot f \qquad [\text{Eq. 1}]$$

where D+A indicates donor- and acceptor-labeled samples, $F_{STRITC}$ is the STRITC emission per cell, corrected for D and A spillover into the STRITC channel, and $F_{FITC}$ is the FITC fluorescence intensity per cell. s is the ratio of the mean fluorescence intensity of the entire population of cells detected in the FITC channel and STRITC channel for samples labeled with donor alone, and $$f = \{[f(A)a(D)]/[f(D)a(A))]-1\}^{-1} \quad [\text{Eq. 2}]$$

where a and f refer, respectively, to the absorbance at 488 nm and the 488 nm-excited, integrated fluorescence at wavelengths >590 nm measured for donor- or acceptor-labeled cells in suspension.

The energy transfer efficiency, E, is related to the distance, R, between donor and acceptor as:

$$E = \{[R^6/R_0(2/3)^6]+1\}^{-1} \quad [\text{Eq. 3}]$$

where $R_0(2/3)$ is the Förster critical distance, or the distance at which the efficiency of transfer between donor and acceptor is 50%, assuming unrestricted orientation of donor and acceptor relative to the labeled macromolecule (Fairclough and Cantor, 1978). The $R_0(2/3)$ for the dye pair, FITC and TRITC, used in our experiments is 40 Å. Thus, E should be a sensitive measurement of distances from 20 to 60 Å. However, for assemblies on the cell surface labeled indirectly with chromophore-conjugated mAbs, E can only be used at best to compare distances, that is, to estimate changes in proximity, between the labeled epitopes (Chuck et al, 1990).

In equation 1, the parameter is governed by the optics used to discriminate FITC and STRITC fluorescence, the sensitivity of the photomultipliers and the path of the emitted light from the flow stream to the FITC and STRITC channels, while the parameter f is governed by the spectral properties of the dye-conjugated mAbs as well as the spectral properties of the cells to which they are bound. Therefore, s and f are constant within each experiment, and $$E = [F_{STRITC}(D+A)/F_{FITC}(D+A)] \cdot k \quad [\text{Eq. 4}]$$

In order to follow changes in energy transfer efficiency, we define $E'(t) = E(t)/E_0$, where E(t) is the energy transfer efficiency per cell obtained for HPB-ALL following modulation at 37° C. for t min and $E_0$ is the energy transfer efficiency per cell obtained for unmodulated cells. E is inversely proportional to the distance separating donor and acceptor (Eq. 3). However, it is essential to bear in mind that, on a flow system, fluorescence intensities are detected as signals integrated over the entire cell, such that $F_{STRITC}$ is a function of $n_{D+A}$, the number of donor- and acceptor-labeled assemblies per cell and $F_{FITC}$ is a function of $n_D$, the number of donor-labeled epitopes per cell. When $n_{D+A} \neq n_D$ and $n_{D+A}/n_D \neq k$, it is often impossible to differentiate between changes in proximity and changes in the number of assemblies relative to the number of donor-labeled epitopes on the cell surface. Therefore, it is more appropriate to interpret changes in E' as changes in CD4-TCR association following CD4 ligation at 0° C. and 37° C.

Results and Discussion

Bispecific Construct Binding Curves

Shown in FIG. 13A is the binding of different concentrations of DNA-antibody constructs (anti-Leu3a Fab'-single stranded 32mer (A) (SEQ ID NO:1) conjugate, T40/25 Fab'-single stranded 32mer (B) (SEQ ID NO:2) conjugate, annealed complementary conjugate product (AB) (SEQ ID NOS:1 and 2) and the T40/25 F(ab')₂ antibody conjugate to HPB-ALL cells around the saturation point. The theoretical ½A (SEQ ID NO:1)+½B (SEQ ID NO:2) binding is also shown. FACS detection was achieved via secondary staining by FITC-GαMIgG (relative flyorescence was plotted against antibody concentration). As shown, all constructs bound saturable sites (up to at least 100 μg/ml, data not shown) arguing for unique receptor targets. In addition, binding of T40/25 Fab'-single stranded 32mer (B) (SEQ ID NO:2) conjugate approximated that of T40/25 F(ab')₂ antibody fragment showing that DNA-conjugation caused little deleterious effect on binding. Binding of the bispecific construct formed by annealing the anti-Leu3a Fab'-single stranded 32mer (A) (SEQ ID NO:1) to the complementary T40/25 Fab'-single stranded 32mer (B) appeared to equal the sum of the A and B (SEQ ID NO:2) binding curves. In making this determination one must note that at each concentration, AB (SEQ ID NOS:1 and 2) is made up of ½A (SEQ ID NO:1) and ½B, (SEQ ID NO:2) not simply A+B (SEQ ID NOS:1 and 2). In Example 2, it was determined that these conjugates most probably annealed to form double-stranded species. If so, then the AB (SEQ ID NOS:1 and 2) binding curve may represent bivalent binding, as a higher level of staining would be expected if these bispecific constructs each bound by only one end. However, we cannot rule out the possibility that the secondary antibody simply had less binding sites on the AB conjugate than on the individual A and B conjugates cannot be ruled out.

FIG. 13B shows the binding of the hybrid antibodies to HPB-ALL cells near the saturation point. Also shown in FIG. 13B is the binding curve of the theoretical [CD3,X] species which only binds CD3. [CD3,4], [CD3,4B], [CD3,8] and the parent [CD3,3] antibody all appeared to bind saturable epitopes (up to at least 250 μg/ml, data not shown). Since a sub-class insensitive secondary antibody was used here, some gross comparisons can be made. As above, in making these comparisons one must remember that [CD3,X] is made up ½ 3 and ½ X and not simply 3+X. As shown, [CD 3,8] apparently bound to the same extent as the theoretical [CD3,X] species. In comparison, both [CD3,4] and [CD3, 4B] bound comparably, but less than the theoretical [CD3,X] species. Thus [CD3,8] either bound wholly by its anti-CD3 end, or bivalently with less anti-CD3 affinity. On the other hand, [CD3,4] and [CD3,4B] both appeared to have markedly reduced affinity for CD3. However, if the 3,4 species were to bind both CD4 and the TCR simultaneously, then less binding would be expected because CD4 is less abundant on the cell surface than CD3 (data not shown).

Bispecific Construct-Induced Receptor Modulations

FIGS. 14A and 14B demonstrate the CD4 and CD3 modulation capability of different concentrations of DNA-antibody conjugates (2,5 and 10 μg/ml which correspond to sub-saturation, saturation and super-saturation from FIG. 13A after 0° C. pre-binding, unbound antibody removal, and then 37° C. incubation for 30 min. In all experiments, saturation and super-saturation should represent the same plateau values from FIG. 13. Cells were subsequently stained with FITC-OKT4 and TRITC-OKT3 for 30 min at 0° C. All fluorescence values are normalized to the amount of staining in the absence of modulating antibody at 0° C. 0° C. (closed bars) and 37° C. (open bars) effects are shown. In FIG. 14A, CD4 modulations with the following constructs, all at equal antibody protein concentrations, are shown: anti-Leu3a Fab'-single stranded 32mer (A) (SEQ ID NO:1), T40/25 Fab'-single stranded 32mer(B) (SEQ ID NO:2), the annealed AB (SEQ ID NOS:1 and 2) conjugate and T40/25 F(ab')₂. At all 3 concentrations, the anti-CD4 containing A (SEQ ID NO:1) conjugate did not modulate CD4, while the anti-TCR containing B (SEQ ID NO:2) conjugate did modulate CD4. To explain this, we note that, as shown in Table 2, the B (SEQ ID NO:2) conjugate significantly blocks anti-CD4 staining. The AB (SEQ ID NOS:1 and 2) conjugate modulated CD4 even more than the B conjugate did, indicating that some synergy is imparted by the A (SEQ ID NO:1) portion of the conjugate. Again, in interpreting this data, one must remember that the double-stranded AB (SEQ ID NOS:1 and 2) conjugate is actually ½ A (SEQ ID NO:1)+½ B, (SEQ ID NO:2) and not simply A+B. Thus the AB synergy in modulating CD4 is quite striking indeed. Interestingly, although T40/25 Fab'-32B (SEQ ID NO:2) significantly modulated CD4, T40/25 F(ab')$_2$ was not able to.

FIG. 14B displays the CD3 modulations. As expected, T40/25 F(ab')$_2$ modulated CD3 to the greatest extent, and anti-Leu3a Fab'-32A did not modulate CD3 at all. However, both T40/25 Fab'-32B (SEQ ID NO:2) and the AB (SEQ ID NOS:1 and 2) structure both modulated CD3 to approximately the same extent at all 3 concentrations tested. Thus, although AB (SEQ ID NOS:1 and 2) modulated more CD4 than A (SEQ ID NO:1) or B (SEQ ID NO:2), it only modulated CD3 equally as well as B (SEQ ID NO:2), indicating the existence of a large pool of CD3 that is susceptible to modulation without the need for cross-linking. It cannot be exlained why in some cases, most notably the AB (SEQ ID NOS:1 and 2) conjugates, treatment with modulating conjugate at 0° C. results in increased colored antibody binding and possible associated structural change in the receptors. Not much modulation difference is seen for the 3 concentrations, perhaps indicative of their closeness to the saturation point.

FIGS. 14C and 14D show the results of the same experiments done with the [CD3,3], [CD3,4], [CD3,4B] and [CD3,8] hybrid antibodies (5,15 and 30 μg/ml which correspond to sub-saturation, saturation and super-saturation from FIG. 13B). Staining in these experiments was done with FITC-anti-Leu3a and TRITC-T40/25 for 30 min at 0° C. In FIG. 14C, we observe that CD4 modulation by [CD3,4 and 4B] was poor at sub-saturation (~5%), but much better at the 2 other concentrations (~15%). All of the hetero-hybrids, [CD3,4 and 4B] more so than [CD3,8], all modulated CD4 to much greater extents than [CD3,3]. Although the possibility that CD4 and CD8 were physically associated (Gallagher et al., 1989) cannot be ruled out, another likely possibility is that anti-CD8 caused co-modulation of CD4 via a common second messenger system acting through, for example, p56$^{lck}$ which is known to associate with both CD4 and CD8 (Veillette et al., 1988).

FIG. 14D displays the TCR modulation results. Neither the parent [CD3,3] hybrid nor the hetero-bispecific hybrids appeared to significantly modulate the TCR. This result is especially peculiar considering FIG. 14C in which the hetero-hybrids could significantly modulate CD4 in comparison to the [CD3,3] parent. These results are inconsistent with simple CD4:TCR complex modulation. In addition, all hybrids, especially [CD3,3], caused relatively large increases in TRITC-T40/25 binding at 0° C., perhaps indicative of conformational change. More information must be obtained on the [CD3,3] parent to interpret these data (Wong, personal communication).

Energy Transfer

Shown in Table 3 are the calculated energy transfer efficiencies, E' defined as above. At 0° C., if CD4 is indeed associated with the TCR and their separation is within the span of the double-stranded DNA cross-linker, (SEQ ID NOS:1 and 2) we would expect to see greatest change in E' upon treatment of cells with anti-CD3/anti-CD4 bispecific constructs. At 0° C. only the AB construct appeared to be effective, with greatest increase in E', here representative of CD4 D3 (FITC-OKT4) and CD3ε association, seen at the saturating concentration (1.36 vs. 1.06 and 1.19). This observed increase indicates actual CD4-TCR cross-linking. After treatment of cells for 30 min at 37° C., all of the T40/25 containing constructs, namely B, (SEQ ID NO:2) AB (SEQ ID NOS:1 and 2) and F(ab')$_2$ but not A (SEQ ID NO:1) all caused significant decreases in E', with F(ab')$_2$ being the most effective. However, referring to FIGS. 16A and 16B, these observed decreases may have been somewhat due to different rates of CD4, TCR, and CD4:TCR complex modulation.

At 0° C. all of the hybrid antibodies, except [CD3,8], at all 3 concentrations tested caused significant increases in E', here indicative of CD4 D1 (FITC-anti-Leu3a) and TCR idiotypic region (TRITC-T40/25) association. As shown in FIG. 14D, [CD3,X] may have caused significant conformational changes upon binding at 0° C., making these results impossible to interpret. That is, the distinction between CD4-TCR cross-linking and TCR conformational change could not be easily made. In general, at 37° C., E' was observed for the most part to decrease from 0° C. values for all hybrid antibodies tested. However, again in addition to the possible hybrid antibody-induced conformation changes, these observed decreases may have been somewhat due to different rates of CD4, TCR, and a CD4:TCR complex modulation.

In summary, we have shown that the double-stranded DNA cross-linked hetero-Fab' anti-CD4/anti-TCR construct can bind, modulate and cross-link CD4 and TCR, and compares favorably in these respects to standard hybrid antibodies. Moreover cross-linking was observed to take place within the span 32 base pair length of cross-linking DNA (SEQ ID NOS:1 and 2) (theoretically 108.8 Å).

TABLE 3

Change in energy transfer efficiency, E', caused by different concentrations of bispecific DNA-antibody conjugates and hybrid bispecific antibodies at 0° C. and 37° C. after treatment of cells for 30 min. E' was calculated as described above.

| Treatment | E' (sub-saturation→saturation→super-saturation) | |
|---|---|---|
| | 0° C. | 37° C. |
| OKT4→OKT3 (FITC→TRITC) | | |
| None | 1.00 | |
| A (SEQ ID NO: 1) | 0.89→1.02→0.95 | 1.04→1.10-1.00 |
| B (SEQ ID NO: 2) | 0.90→0.98→0.95 | 0.76→0.76→0.69 |
| AB (SEQ ID NOS: 1 and 2) | 1.06→1.36→1.19 | 0.45→0.76→0.64 |
| F | 0.93→0.97→0.97 | 0.45→0.76→0.64 |
| Anti-Leu3a→T40/25 (FITC→TRITC) | | |
| None | 1.00 | |
| 3,3 | 1.16→1.35→1.10 | 0.94→1.08→0.87 |
| 3,4 | 1.12→1.21→1.14 | 1.12→1.05→1.09 |
| 3,4B | 1.15→1.18→1.30 | 1.33→1.01→0.96 |
| 3,8 | 0.94→1.04→0.96 | 0.97→0.90→0.80 |

In experiments involving anti-Leu3a Fab'-single-stranded 32mer (A) (SEQ ID NO:1) conjugate, the T40/25 Fab'-single-stranded 32mer (B) (SEQ ID NO:2) conjugate, the annealed complementary conjugate product AB, (SEQ ID NOS:1 and 2) and the T40/25 F(ab')$_2$ antibody fragment (F), energy transfer efficiency from FITC-OKT4 to TRITC-OKT3 was calculated.

In experiments involving [CD3,3], [CD3,4], [CD3,4B] and [CD3,8] hybrid antibodies, energy transfer efficiency from FITC-anti-Leu3a to TRITC-T40/25 was calculated.

Close association of both CD4 and the TCR appears to be important for cell triggering as this and other studies have shown. Such a conclusion is not unexpected as both receptors are known to have binding sites for mutually exclusive epitopes on the MHC II molecule. In addition, as described in this example, the energy transfer technique has provided proof of a non-random CD4-TCR association on the plasma membrane. However, the role of CD4 in the activation process is not clear, as both positive and negative signaling have been demonstrated. Of course, both positive and negative signaling may be physiologically relevant, depending on the circumstance on the cell surface. It was proposed that such differences in signaling function may be triggered by different separations (which can be detected using the energy transfer technique described above) of the CD4 and TCR epitopes seen by MHC II, perhaps due to engagement of complexed and uncomplexed CD4 and TCR. This would be consistent with the contention that CD4-MHC recognition without the TCR leads to energy (reviewed in Janeway, 1988). If so, then the bispecific antibody structures described here will permit study of the CD4:TCR complex. Both positive and negative signaling may be effected by triggering via either closely or more distantly spaced anti-CD4 and anti-TCR Fab' antibody fragments, respectively, too determine the role of separation. The hope is to turn on and off T cells at will, perhaps even in a therapeutic manner, and thus selectively alter the immune system.

Probably the greatest value of the CD4:TCR complex work of the invention is its contribution to the establishment of a structural model for T cell activation both in the thymus and in the periphery. The HPB-ALL T cell used in the examples is CD4+CD8+ and thought to represent an immature stage of development. It was observed that when the TCR was engaged at physiological temperature, the idiotypic region of the TCR became more closely associated with CD4, while CD3 dissociated from both CD4 and the TCR. The latter result is unexpected considering that TCR engagement should lead to increased signaling via CD3, and thus an increase in CD3-TCR association would be anticipated. However, in interpreting this result, it should be remembered that CD4 may also be important to the activation process. If so, then it can be proposed that to counter this negative effect of CD3 dissociation, the TCR becomes more intimate with CD4, which may have some positive signaling qualities. As recently discussed by Haughn et al. (1992), one such quality may be to bring the p56$^{lck}$ tyrosine kinase closer to that TCR and make it available for signaling. Furthermore, if cells were treated with anti-CD4 as in this study with anti-Leu3a and OKT4, a negative signaling state would be expected to be induced as the antibody may serve to sequester CD4 from the TCR. Consistent with this notion, a decreased CD4-TCR association after treatment of HPB-ALL with anti-CD4 was observed. Extending this scenario to the in vivo antigen recognition process, in low affinity presentor-effector cell interactions, compared to high affinity situations, more free MHC II may be available to bind and sequester CD4 from the TCR, thus leading to a reduced level of activation. In addition to HPB-ALL, CD4:TCR complexes on mature CD4+lymphocytes have also been observed.

In conclusion, the DNA conjugates of this invention provide new methods to dissect structural and functional relationships between individual components of multi-molecular assemblies on cell surfaces.

EXAMPLE 4

Immuno-PCR with a bis(Fab')-DNA conjugate

This example uses a bis(Fab')-DNA conjugate prepared in the manner described in Examples 2 and 3 except that antibodies from which the Fab' fragments are derived differ from those of the previous examples and the DNA strands are about 60 bases long. The F(ab')$_2$ fragments of this assay are obtained by pepsin cleavage of a first antibody (Aby-1) and a second antibody (Aby-2). The conjugate therefore contains two different Fab' fragments, Fab'-1 and Fab'-2 which bind antigen-1 (Ag-1) and antigen-2 (Ag-2), respectively. Each of these two Fab' fragments is covalently attached to the 5'-terminus of one strand of a double-strand linker DNA. Thus, two different Fab' fragments are located at both termini of the linker DNA, in which a recognition site for a restriction endonuclease is present. This assay is performed to test if the two antigens, Ag-1 and Ag-2, are present in the sample.

The sample solution to be tested is applied to the wells of a microtiter plate. The microtiter plate is incubated at 4° C. overnight to immobilize molecules in the sample solution on the surface of the wells. After a brief washing of the plate with TBS (Tris-buffered saline), the microtiter plate is incubated with non-fat dried milk dissolved in TBS to block reactable sites on the surface of the wells. After the blocking, the wells are briefly washed with ETBS (TBS containing EDTA). The addition of EDTA is indispensable to avoid the digestion of the linker DNA by any contaminating nucleases. Then, the bis(Fab')-DNA conjugate in ETBS is applied to each well, and allowed to bind to antigens immobilized on the surface of the wells. Unreacted bis(Fab')-DNA conjugate is removed by washing the microtiter plate with ETBS. At this stage, each of the bound bis(Fab')-DNA conjugates binds to either Ag-1 or Ag-2, or to both Ag-1 and Ag-2.

A restriction endonuclease corresponding to the restriction enzyme recognition site present in the DNA is applied to each well after the addition of an appropriate reaction solution for the restriction endonuclease, and allowed to digest the linker DNA molecule of the bis(Fab')-DNA conjugate. After the digestion, the microtiter plate is washed extensively with ETBS. When the conjugate binds either Ag-1 or Ag-2, one of the Fab' fragments with a half of the digested linker DNA is removed by washing. Both Fab' fragments remain bound to antigens only when the conjugate binds both Ag-1 and Ag-2 simultaneously. Then, DNA ligase is added to the wells to religate the digested linker DNA, after the addition of an appropriate ligation solution to wells. When a bis(Fab')-DNA conjugate binds both Ag-1 and Ag-2, religation of the linker DNA occurs. However, when one of the paired Fab' fragments is removed, no ligation reaction would occur because of the absence of the other half of the linker DNA. Then, PCR is performed on the microtiter plate wells under standard conditions to amplify the religated linker DNA. A set of primers, which hybridize to the linker DNA flanking the restriction enzyme recognition sequence, are used. The resulting PCR product is analyzed by an appropriate method, such as gel electrophoresis. The PCR product can be produced only when the bis(Fab')-DNA conjugate binds two different antigens simultaneously and the linker DNA is religated. Thus, the presence of the specific PCR product demonstrates that two antigens, Ag-1 and Ag-2, are present in the sample. Further, this method cuts down on the noise and background in immuno-PCR. When only one antigen is present in the sample, a shorter PCR product, which corresponds to the length from one of the primer-annealing site to the restriction endonuclease recognition site is produced. However, such PCR products can be discriminated from the full-length PCR product produced from the religated linker DNA. In addition, the amount of such PCR products is much smaller than the full-length PCR product, because one Fab' fragment with a half of the linker DNA allows only linear PCR amplification of a portion of the linker DNA, not the exponential PCR amplification which occurs with the religated linker DNA.

This type of assay also allows for coincident detection of pairs of epitopes on antigens or organic molecules where individual monoclonal antibody discrimination is insufficient for an accurate analysis.

All publications mentioned in this specification are herein incorporated by reference to the same extent as if each individual publication was specifically and individually indicated to be incorporated by reference.

The invention now being fully described, it will be apparent to one of ordinary skill in the art that many changes and modifications can be made thereto without departing from the spirit or scope of the appended claims.

BIBLIOGRAPHY

Bennett, R. M., Gabor, G. T., and Merritt, M. M. (1985). DNA binding to human leukocytes. Evidence for a receptor-mediated association, internalization, and degradation of DNA. J. Clin. Invest. 76, 2182–2190.

Beyers, A. D., Spruyt, L. L., and Williams, A. F. (1992). Molecular associations between the T-lymphocyte antigen receptor complex and the surface antigens CD2, CD4, or CD8 and CD5. Proc. Natl. Acad. Sci. U.S.A. 89, 2945–2949.

Bird, R. E., Hardman, K. D., Jacobsen, J. W., Johnson, S., Kaufman, B. M., Lee, S. M., Lee, T., Pope, S. H., Riordan, G. S., and Whitlow, M. (1988). Single-chain antigen-binding proteins. Science 242, 423–426.

Brennan, M., Davison, P. F., and Paulus, H. (1985). Preparation of bispecific; antibodies by chemical recombination of monoclonai immunoglobulin $G_1$ fragments. Science 229, 81–83.

Burgess, K. E., Oddysseos, A. D., Zalvan, C., Druker, B. J., Anderson, P., Schlossman, S. F., and Rudd, C. E. (1991). Biochemical identification of a direct physical interaction between the CD4:$p56^{lck}$ and $T_i$ (TcR)/CD3 complexes. Eur. J. Immunol. 21, 1663–1668.

Chuck, R. S., Cantor, C. R., and Tse, D. B. (1990). CD4-T-cell receptor complexes on human leukemia T cells. Proc. Natl. Acad. Sci. U.S.A. 87, 5021–5025.

Cohen, C. (1992). Mounting a targeted strike on unwanted immune responses. Science 257, 751.

Connolly, B. A., and Rider, P. (1985). Chemical synthesis of oligonucleotide containing a free sulphydryl group and subsequent attachment of thiol specific probes. Nucleic Acids Res. 13, 4485–4502.

Cosgrove, D., Gray, D., Dietrich, A., Kaufman, J., Lemeur, M., Benoist, C., and Mathis, D. (1991). Mice lacking MHC class II molecules. Cell 66, 1051–1066.

Davis, B. J. (1964). Disc electrophoresis II. Method and application to human serum proteins. Ann. N. Y. Acad. Sci. 121, 404–427.

Doyle, C., and Strominger, J. L. (1987). Interaction between CD4 and class II MHC molecules mediate cell adhesion. Nature 330, 256–259.

Ellegren, H., and Laas, T. (1989). Size-exclusion chromatography of DNA restriction fragments. Fragment length determinations and a comparison with the behavior of proteins in size-exclusion chromatography. J. Chromatogr. 467, 217–226.

Fairclough, R. H., and Cantor, C. R. (1978). The use of singlet-singlet energy transfer to study macromolecular assemblies. Methods Enzymol. 48, 347–379.

Fleischer, B., and Schrezenmeier, H. (1988). Do CD4 or CD8 molecules provid a regulatory signal in T-cell activation? Immunol. Today 9, 132–134.

Gallagher, P. F., de St. Groth, B. F., and Miller, J. F. A. P. (1989). CD4 and CD8 molecules can physically associate with the same T-cell receptor. Proc. Natl. Acad. Sci. U.S.A. 86, 10044–10048.

Glennie, M. J., McBride, H. M., Worth, A. T., and Stevenson, G. T. (1987). Preparation and performance of bispecific $F(ab'_\gamma)_2$ antibody containing thioether-linked $Fab'_\gamma$-fragments. J. Immunol. 139, 2367–2375.

Green, N. M. (1969). Electron microscopy of the immunoglobulins. Adv. Immunol. 11, 1–30.

Greenspan, N. S., Dacek, D. A., and Cooper, L. J. N. (1989). Cooperative binding of two antibodies to independent antigens by an Fc-dependent mechanism. FASEB J. 3, 2203–2207.

Hagerman, P. J. (1988). Flexibility of DNA. Annu. Rev. Biophys. Biophysical Chem. 17, 265–286.

Haque, S., Saizawa, K., Rojo, J., and Janeway, C. A. Jr. (1987). The influence of valence of the functional activities of monoclonal anti-L3T4 antibodies. Discrimination of signaling from other effects. J. Immunol. 139, 3207–3212.

Haughn, L., Gratton, S., Caron, L., Sékaly, R.-P., Veillette, A., and Julius, M. (1992). Association of tyrosine kinase $p56^{lck}$ with CD4 inhibits the induction of growth through the $\alpha\beta$ T-cell receptor. Nature 358, 328–331.

Huse, W. D., Sastry, L., Iverson, S. A., Kang, A. S., Alting-Mees, M., Burton, D. R., Benkovic, S. J., and Lerner, R. A. (1989). Generation of a large combinatorial library of the immunoglobulin repertoire in phage lambda. Science 246, 1275–1281.

Janeway, C. A. Jr. (1988). T-cell development. Accessories or coreceptors? Nature 335, 208–210.

Janeway, C. A. Jr., Haque, S., Smith, L. A., and Saizawa, K. (1987). The role of murine L3T4 molecule in T cell activation: differential effects of anti-L3T4 on activation by monoclonal antireceptor antibodies. J. Mol. Cell. Immunol. 3, 121–131.

Jung, G., Freimann, U., Von Marschall, Z., Reisfeld, R. A., and Wilmanns, W. (1991). Target cell-induced T cell activation with bi- and trispecific antibody fragments. Eur. J. Immunol. 21, 2431–2435.

Kostelny, S. A., Cole, M. S., and Tso, J. Y. (1992). Formation of a bispecific antibody by the use of leucine zippers. J. Immunol. 148, 1547–1553.

Krangel, M. S. (1987). Endocytosis, and recycling of the T3-T cell receptor complex. The role of T3 phosphorylation. J. Exp. Med. 165, 1141–1159.

Laemmli, U. K. (1970). Cleavage of structural proteins during the assembly of the head of bacteriophage T4. Nature 222, 680.

Ledberter, J. A., June, C. H., Grosmaire, L. S., and Rabinovitch, P. S. (1987). Cross-linking of surface antigens causes mobilization of intracellular ionized calcium in T lymphocytes. Proc. Natl. Acad. Sci. U.S.A. 84, 1384–1388.

Ledbetter, J. A., Norris, N. A., Grossmann A., Grosmaure, L. S., June, C. H., Uckun, F. M., Cosand, W. L., and Rabinovitch, P. S. (1989). Enhanced transmembrane signaling activity of monoclonal antibody heteroconjugates suggests molecular interactions between receptors on the T cell surface. Molec. Immunol. 26, 137–145.

Ledbetter, J. A., Schieven, G. K. L., Kuebelbeck, V. M., and Uckun, F. M. (1991). Accessory receptors regulate coupling of the T-cell receptor complex to tyrosine kinase activation and mobilization of cytoplasmic calcium in T-lineage acute lymphoblastic leukemia. Blood 77, 1271–82.

Ledbetter, J. A., Tonks, N. K., Fischer, E. H., and Clark, E. A. (1988). CD45 regulates signal transduction and lymphocyte activation by specific association with receptor molecules on T or B cells. Proc. Natl. Acad. Sci. U.S.A. 85, 8628–8632.

Lenschow, D. J., Zeng, Y., Thistlethwaite, J. R., Montag, A., Brady, W., Gibson, M. G., Linsley, P. S., and Bluestone, J. A. (1992). Long-term survival of xenogeneic pancreatic islet grafts induced by CTLA4Ig. Science 257, 789–792.

Linsley, P. G., Wallace, P. M., Johnson, J., Gibson, M. G., Greene, J. L., Ledbetter, J. A., Singh, C., and Tepper, M. A. (1992). Immunosuppression in vivo by a soluble form of the CTLA-4 T cell activation molecule. Science 257, 792–795.

Loke, S. L., Stein, C. A., Zhang, X. H., Mori, K., Nakanishi, M., Subasinghe, C., Cohen, J. S., and Neckers, L. M. (1989). Characterization of oligonucleotide transport in living cells. Proc. Natl. Acad. Sci. U.S.A. 86, 3474–3478.

Miceli, M. C., von Hoegen, P., and Parnes, J. R. (1991). Adhesion versus coreceptor function of CD4 and CD8: role of the cytoplasmic tail in coreceptor activity. Proc. Natl. Acad. Sci. U.S.A. 88, 2623–2627.

Milstein, C., and Cuello, A. C. (1983). Hybrid hybridomas and their use in immunohistochemistry. Nature 305, 537–540.

Mittler, R. S., Goldman, S. J., Spitalny, G. L., and Burakoff, S. J. (1989a). T-cell receptor CD4 physical association in a murine T-cell hybridoma: induction by antigen receptor ligation. Proc. Natl. Acad. Sci. U.S.A. 86, 8531–8535.

Mittler, R. S., Rankin, B. M., and Kiener, P. A. (1991). Physical associations between CD45 and CD4 or CD8 occur as late activation events in antigen receptor-stimulated human T cells. J. Immunol. 147, 3434–3440.

Nisonoff, A., Hopper, J. E., and Spring, S. B. (1975). The Antibody Molecule (Academic, New York), pp. 209–237.

Olson, W. K., and Srinivasan, A. R. (1988). The translation of DNA primary base sequence into three-dimensional structure. Comp. Applic. Bios. 4, 133–142.

Parham, P. (1983). On the fragmentation of monoclonal IgG1, IgG2a, and IgG2b from BALB/c mice. J. Immunol. 131, 2895–2902.

Rahemtulla, A., Fung-Leung, W. P., Schilham, M. W., Kúndig, T. M., Sambhara, S. R., Narendran, A., Arabian, A., Wakeham, A., Paige, C. J., Zinkernagel, R. M., Miller, R. G., and Mak, T. W. (1991). Normal development and function of CD8+ cells but markedly decreased helper cell activity in mice lacking CD4. Nature 353, 180–184.

Samelson, L. E., Phillips, A. F., Luong, E. T., and Klausner, R. D. (1990). Association of the fyn protein kinase with the T-cell antigen receptor. Proc. Natl. Acad. Sci. U.S.A. 87, 4358–4362.

Saragovi, H. U., Fitzpatrick, D., Raktabutr, A., Nakanishi, H., Kahn, M., and Greene, M. I. (1991). Design and synthesis of a mimetic from an antibody complementarity determining region. Science 253, 792–795.

Sastry, L., Alting-Mees, M., Huse, W. D., Short, J. M., Sorge, J. A., Hay, B. N., Janda, K. D., Benkovic, S. J., and Lerner, R. A. (1989). Cloning of the immunological repertoire in *Eschericia coli* for generation of monoclonal catalytic antibodies: construction of a heavy chain variable region-specific cDNA library. Proc. Natl. Acad. Sci. U.S.A. 86, 5728–5732.

Schrezenmeier, H., and Fleischer, B. (1988). A regulatory role for the CD4 and CD8 molecules in T cell activation. J. Immunol. 141, 398–403.

Segal, D. M., and Hurwitz, E. (1976). Dimers and trimers of immunoglobulin G covalently cross-linked with a bivalent affinity label. Biochemistry 15, 5253–5258.

Telfner, J. C., and Rudd, C. E. (1991). A 32-kD GTP-binding protein associated with the CD4-p56$^{lck}$ and CD8-p56$^{lck}$ T cell receptor complexes. Science 254, 439–441.

Veillette, A., Bookman, M. A., Horak, E. M., and Bolen, J. B. (1988). The CD4 and CD8 T cell surface antigens are associated with the internal membrane tyrosine-protein kinase p56$^{lck}$. Cell 55, 301–308.

Volarevic, S., Burns, C. M., Sussman, J. J., and Ashwell, J. D. (1990). Intimate association of Thy-1 and the T-cell antigen receptor with the CD45 tyrosine phosphatase. Proc. Natl. Acad. Sci. U.S.A. 87, 7085–7089.

Ward, E. S., Gussow, D., Griffiths, A. D., Jones, P. T., and Winter, G. (1989). Binding activities of a repertoire of single immunoglobulin variable domains secreted from *Eschericia coli*. Nature 341, 544–546.

Williams, A. L. Jr., and Tinoco, I. Jr. (1986). A dynamic programming algorithm for finding alternative RNA secondary structures. Nuc. Acids Res. 14, 299–315.

Wong, J. T., Pinto, C. E., Gifford, J. D., Kurnick, J. T., and Kradin, R. L. (1989). Characterization of the CD4+ and CD8+ tumor infiltrating lymphocytes propagated with bispecific monoclonal antibodies. J. Immunol. 143, 3404–3411.

Yakubov, L. A., Deeva, E. A., Zarytova, V. F., Ivanova, E. M., Ryte, A. S., Yurchenko, L. V., and Vlassov, V. V. (1989). Mechanism of oligonucleotide uptake by cells: involvement of specific receptors? Proc. Natl. Acad. Sci. U.S.A. 86, 6454–6458.

What is claimed is:

1. A method for preparing a double stranded DNA-protein conjugate comprising
    (a) preparing a first thiolated single stranded DNA, wherein said first thiolated single stranded DNA is
        (1) about 10 to 100 bases in length, and
        (2) thiolated at either the 3' or 5' end;
    (b) preparing a second thiolated single stranded DNA, said first and second thiolated single DNA strand being complementary to each other, and wherein said second thiolated single stranded DNA is
        (1) about 10 to 100 bases in length, and
        (2) thiolated at the same end as said first thiolated DNA strand;
    (c) reacting said first thiolated DNA strand with a thionitrobenzoate derivatized ligand binding first protein to form a first single stranded DNA-protein conjugate;
    (d) reacting said second thiolated DNA strand with a thionitrobenzoate derivatized ligand binding second protein to form a second single stranded DNA-protein conjugate;
    (e) annealing said first and second single stranded conjugates; and
    (f) recovering the double stranded DNA-protein conjugate product of step (e).

2. The method of claim 1 wherein the derivatized first protein is an antibody to a first CD antigen and the derivatized second protein is an antibody to a different CD antigen.

3. The method of claim 1 wherein said first derivatized protein is an IgG with a first antigen specificity and said second derivatized protein is an IgG with a different antigen specificity.

4. The method of claim 1 wherein said first derivatized protein is a first antibody and said derivatized second protein is a second antibody.

5. The method of claim 4 wherein said first and second antibody have the same antigen specificity.

6. A DNA-protein conjugate prepared according to claim 1.

7. A method for preparing a bis(Fab')-DNA conjugate comprising
    (a) preparing a first thiolated single stranded DNA, wherein said first thiolated single stranded DNA is
        (1) about 10 to 100 bases in length, and
        (2) thiolated at either the 3' or 5' end;
    (b) preparing a second thiolated single stranded DNA, said first and second thiolated single DNA strand being complementary to each other, and wherein said second thiolated single stranded DNA is
        (1) about 10 to 100 bases in length, and
        (2) thiolated at the same end as said first thiolated DNA strand;
    (c) reacting said first thiolated DNA strand with a thionitrobenzoate derivatized first antibody Fab' fragment to form a first single stranded DNA-Fab' conjugate;
    (d) reacting said second thiolated DNA strand with a thionitrobenzoate derivatized second antibody Fab' fragment to form a second single stranded DNA-Fab' fragment conjugate;
    (e) annealing said first and second single stranded conjugates, and
    (f) recovering the bis(Fab')-double stranded DNA conjugate product of step (e).

8. The method of claim 7 wherein said derivatized first antibody Fab' fragment is an anti-CD4 Fab' fragment and said derivatized second antibody Fab' fragment is an anti-TCR Fab' fragment.

9. A bis(Fab')-DNA conjugate prepared according to claim 7.

10. A bis-protein DNA conjugate comprising a ligand binding first protein cross-linked by a double stranded DNA to a ligand binding second protein, wherein said ligand binding first protein is linked to a 5' end and said ligand binding second protein is linked to the other 5' end or said ligand binding first protein is linked to a 3' end and said ligand binding second protein is linked to the other 3' end of said double stranded DNA via disulfide bonds, wherein said double stranded DNA is about 10 to about 100 base pairs in length, and wherein said ligand binding first protein and said ligand binding second protein retain the ability to specifically recognize and bind to their respective ligands when cross-linked to said double stranded DNA and the strands of said double stranded DNA are complementary to each other.

11. The conjugate of claim 10 wherein the ligand binding first protein is a first antibody and the ligand binding second protein is a second antibody.

12. The conjugate of claim 11 wherein the first antibody is an IgG having a binding specificity to a first antigen and the second antibody is an IgG having a binding specificity to a second antigen.

13. The conjugate of claim 11 wherein said first antibody and said second antibody have a binding specificity to the same antigen.

14. The conjugate of claim 10 wherein said ligand binding first protein is a first antibody Fab' fragment and said ligand binding second protein is a second antibody Fab' fragment.

15. A bis-protein DNA conjugate comprising a ligand binding first protein cross-linked by a double stranded DNA to a ligand binding second protein, wherein, via disulfide bonds, said ligand binding first protein is linked to a 5' end and said ligand binding second protein is linked to the other 5' end or said ligand binding first protein is linked to a 3' end and said ligand binding second protein is linked to the other 3' end of said double stranded DNA, and wherein said double stranded DNA is about 10 to about 100 base pairs in length and the DNA strands of said double stranded DNA are complementary to each other.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 32 base pairs
        ( B ) TYPE: nucleic acid ( C ) STRANDEDNESS: single
                ( D ) TOPOLOGY: linear ( i i ) MOLECULE TYPE: cDNA ( i x ) FEATURE:
                ( A ) NAME/KEY: misc_feature
                ( B ) LOCATION: complement (1)
                ( D ) OTHER INFORMATION: /note= "Biotinylation
                        site."

( i x ) FEATURE:
                ( A ) NAME/KEY: misc_feature
                ( B ) LOCATION: complement (13..16)
                ( D ) OTHER INFORMATION: /note= "Mae II restriction
                        site."

( i x ) FEATURE:
                ( A ) NAME/KEY: misc_feature
                ( B ) LOCATION: complement (15..20)
                ( D ) OTHER INFORMATION: /note= "Acc I restriction
                        site."

( i x ) FEATURE:
                ( A ) NAME/KEY: misc_feature
                ( B ) LOCATION: complement (15..20)
                ( D ) OTHER INFORMATION: /note= "Hinc II restriction
                        site."

( i x ) FEATURE:
                ( A ) NAME/KEY: misc_feature
                ( B ) LOCATION: complement (15..20)
                ( D ) OTHER INFORMATION: /note= "Sal I restriction
                        site."

( i x ) FEATURE:
                ( A ) NAME/KEY: misc_feature
                ( B ) LOCATION: complement (16..19)
                ( D ) OTHER INFORMATION: /note= "Taq I restriction
                        site."

( i x ) FEATURE:
                ( A ) NAME/KEY: misc_feature
                ( B ) LOCATION: complement (18..23)
                ( D ) OTHER INFORMATION: /note= "Aat II restriction
                        site."

( i x ) FEATURE:
                ( A ) NAME/KEY: misc_feature
                ( B ) LOCATION: complement (18..23)
                ( D ) OTHER INFORMATION: /note= "Aha II restriction
                        site."

( i x ) FEATURE:
                ( A ) NAME/KEY: misc_feature
                ( B ) LOCATION: complement (18..26)
                ( D ) OTHER INFORMATION: /note= "Tthlll I
                        restriction site."

( i x ) FEATURE:
                ( A ) NAME/KEY: misc_feature
                ( B ) LOCATION: complement (19..22)
                ( D ) OTHER INFORMATION: /note= "Mae II restriction
                        site."

( i x ) FEATURE:
                ( A ) NAME/KEY: misc_feature
                ( B ) LOCATION: complement (24..28)
                ( D ) OTHER INFORMATION: /note= "Mae III restriction
                        site."

( i x ) FEATURE:
                ( A ) NAME/KEY: misc_feature
                ( B ) LOCATION: complement (18..29)
                ( D ) OTHER INFORMATION: /note= "Hph I restriction
                        site."

( i x ) FEATURE:
                ( A ) NAME/KEY: misc_feature
                ( B ) LOCATION: complement (28..32)

(D) OTHER INFORMATION: /note= "First 5 bases of
    MnI I restriction site. Completion of restriction site
    requires any 6 additional bases 3'of this sequence."

(ix) FEATURE:
    (A) NAME/KEY: misc_feature
    (B) LOCATION: complement (1..32)
    (D) OTHER INFORMATION: /note= "Complementary to
        SEQ ID NO:2, bases 1 to 32."

(xi) SEQUENCE DESCRIPTION: SEQ ID NO:1:

ACTATACATC ATACGTCGAC GTCGTCACCT CA　　32

(2) INFORMATION FOR SEQ ID NO:2:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: complement (1)
        (D) OTHER INFORMATION: /note= "Biotinylation
            site."

(ix) FEATURE:
        (A) NAME/KEY: misc_feature
        (B) LOCATION: complement (1..5)
        (D) OTHER INFORMATION: /note= "Last 5 bases in
            MnI I restriction site. Completion of restriction site
            requires any 5 additional bases 5'of this sequence."

(ix) FEATURE:
        (A) NAME/KEY: misc_feature
        (B) LOCATION: complement (4..15)
        (D) OTHER INFORMATION: /note= "Hph I restriction
            site."

(ix) FEATURE:
        (A) NAME/KEY: misc_feature
        (B) LOCATION: complement (5..9)
        (D) OTHER INFORMATION: /note= "Mae III restriction
            site."

(ix) FEATURE:
        (A) NAME/KEY: misc_feature
        (B) LOCATION: complement (11..14)
        (D) OTHER INFORMATION: /note= "Mae II restriction
            site."

(ix) FEATURE:
        (A) NAME/KEY: misc_feature
        (B) LOCATION: complement (7..15)
        (D) OTHER INFORMATION: /note= "Tth111 I
            restriction site."

(ix) FEATURE:
        (A) NAME/KEY: misc_feature
        (B) LOCATION: complement (10..15)
        (D) OTHER INFORMATION: /note= "Aha II restriction
            site."

(ix) FEATURE:
        (A) NAME/KEY: misc_feature
        (B) LOCATION: complement (10..15)
        (D) OTHER INFORMATION: /note= "Aat II restriction
            site."

(ix) FEATURE:
        (A) NAME/KEY: misc_feature
        (B) LOCATION: complement (14..17)
        (D) OTHER INFORMATION: /note= "Taq I restriction
            site."

-continued

```
       ( i x ) FEATURE:
               ( A ) NAME/KEY: misc_feature
               ( B ) LOCATION: complement (13..18)
               ( D ) OTHER INFORMATION: /note= "Sal I restriction
                       site."

( i x ) FEATURE:
               ( A ) NAME/KEY: misc_feature
               ( B ) LOCATION: complement (13..18)
               ( D ) OTHER INFORMATION: /note= "Hinc II restriction
                       site."

( i x ) FEATURE:
               ( A ) NAME/KEY: misc_feature
               ( B ) LOCATION: complement (13..18)
               ( D ) OTHER INFORMATION: /note= "Acc I restriction
                       site."

( i x ) FEATURE:
               ( A ) NAME/KEY: misc_feature
               ( B ) LOCATION: complement (17..20)
               ( D ) OTHER INFORMATION: /note= "Mae II restriction
                       site."

( i x ) FEATURE:
               ( A ) NAME/KEY: misc_feature
               ( B ) LOCATION: complement (1..32)
               ( D ) OTHER INFORMATION: /note= "Complementary to
                       SEQ ID NO:1, bases 1 to 32."

( x i ) SEQUENCE DESCRIPTION: SEQ ID NO:2:

TGAGGTGACG  ACGTCGACGT  ATGATGTATA  GT                                     3 2
```